US009514272B2

(12) United States Patent
Kermani et al.

(10) Patent No.: US 9,514,272 B2
(45) Date of Patent: Dec. 6, 2016

(54) IDENTIFICATION OF DNA FRAGMENTS AND STRUCTURAL VARIATIONS

(71) Applicant: Complete Genomics, Inc., Mountain View, CA (US)

(72) Inventors: Bahram Ghaffarzadeh Kermani, Los Altos, CA (US); Radoje Drmanac, Los Altos Hills, CA (US); Oleg Alferov, Sunnyvale, CA (US)

(73) Assignee: Complete Genomics, Inc., Mountain View, CA (US)

( * ) Notice: Subject to any disclaimer, the term of this patent is extended or adjusted under 35 U.S.C. 154(b) by 739 days.

(21) Appl. No.: 13/649,966

(22) Filed: Oct. 11, 2012

(65) Prior Publication Data

US 2013/0096841 A1   Apr. 18, 2013

Related U.S. Application Data

(60) Provisional application No. 61/546,516, filed on Oct. 12, 2011, provisional application No. 61/623,876, filed on Apr. 13, 2012.

(51) Int. Cl.
*G01N 33/50* (2006.01)
*G06F 19/22* (2011.01)

(52) U.S. Cl.
CPC .................................. *G06F 19/22* (2013.01)

(58) Field of Classification Search
None
See application file for complete search history.

(56) References Cited

U.S. PATENT DOCUMENTS

| | | | |
|---|---|---|---|
| 7,565,346 | B2 | 7/2009 | Fan et al. |
| 2002/0106667 | A1* | 8/2002 | Yamamoto et al. ............. 435/6 |
| 2004/0241730 | A1 | 12/2004 | Yakhini et al. |
| 2010/0112590 | A1 | 5/2010 | Lo et al. |
| 2010/0279883 | A1 | 11/2010 | Sampas et al. |
| 2011/0033854 | A1 | 2/2011 | Drmanac et al. |

OTHER PUBLICATIONS

Zerbina, Daniel, R., et al., "Velvet: Algorithms for de novo short read assembly using de Bruijn graphs," Genome Research, published [online] Mar. 18, 2008, 11 pages.
International Search Report and Written Opinion mailed Nov. 5, 2012 in PCT/US12/33686, 10 pages.
Hormozdiari, et al., "Combinatorial algorithms for structural variation detection in high-throughput sequenced genomes," Genome Research, ePub May 15, 2009, vol. 19, pp. 1270-1279.
International Search Report and Written Opinion mailed Dec. 7, 2012, PCT/US2012/059806, 10 pages.
Lancia, G., et al., "SNPs Problems, Complexity and Algorithms," 2001, Proceedings of the Nineth Annual European Symposium on Algorithms (ESA) Springer, Berlin, 12 pages.
Bansal, V. et al., "HapCUT: an efficient and accurate algorithm for the haplotype assembly problem," Bioinformatics, [online], 2008, vol. 24, pp. i153-i159, retrieved on Mar. 14, 2012, URL: http://bioinformatics.oxfordjournals.org.
Duitama, J. et al., "Fosmid-based whole genome haplotyping of a HapMap trio child: evaluation of Single Individual Haplotyping techniques," Nucleic Acids Research Advance Access published [online] Nov. 18, 2011, 13 pages, retrieved on Mar. 11, 2012, URL: http://nar.oxfordjournals.org.
Suk, E., et al., "A Comprehensively Molecular Haplotype-Resolved Genome of a European Individual," Genome Research, 2011, vol. 21, pp. 672-1685 plus 61 pages of Supplementary Methods.
Cilibrasi, R., et al., "On the complexity of several haplotyping problems," 2005, WABI, vol. 3692 of Lecture Notes in Computer Science, Springer, Berlin, pp. 128-139.

* cited by examiner

*Primary Examiner* — Jason Sims
(74) *Attorney, Agent, or Firm* — Kilpatrick Townsend & Stockton LLP; David B. Raczkowski

(57) ABSTRACT

Various short reads can be grouped and identified as coming from a same long DNA fragment (e.g., by using wells with a relatively low-concentration of DNA). A histogram of the genomic coverage of a group of short reads can provide the edges of the corresponding long fragment (pulse). The knowledge of these pulses can provide an ability to determine the haploid genome and to identify structural variations.

38 Claims, 21 Drawing Sheets

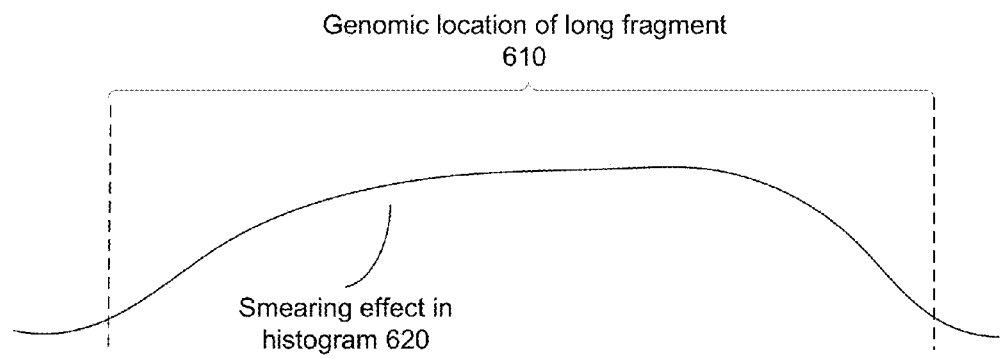
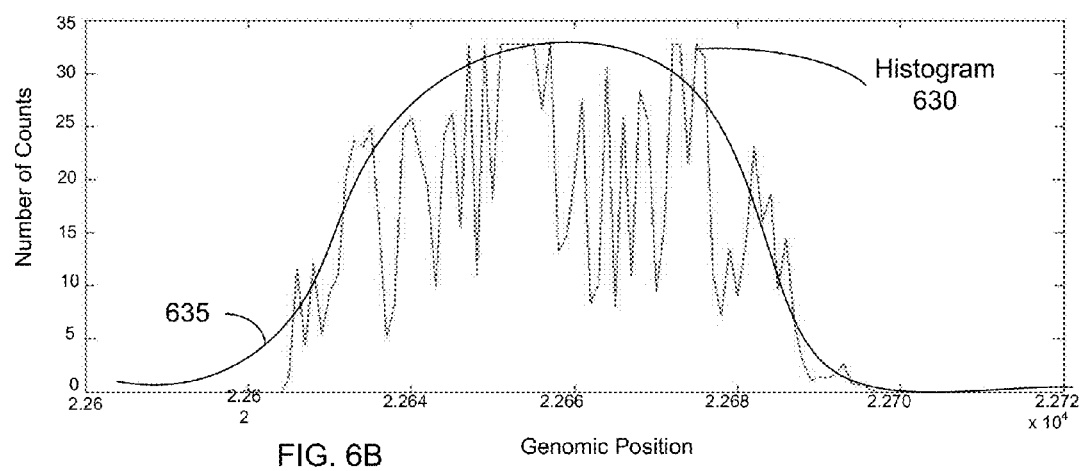
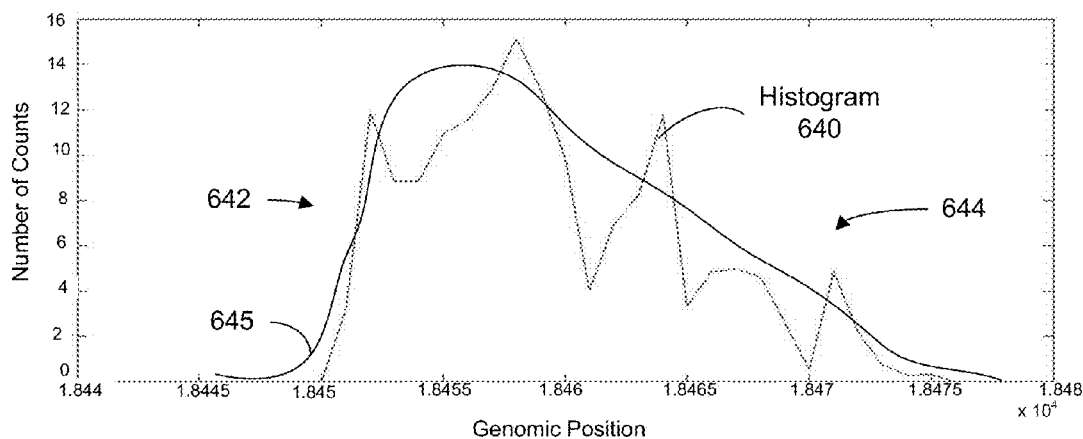

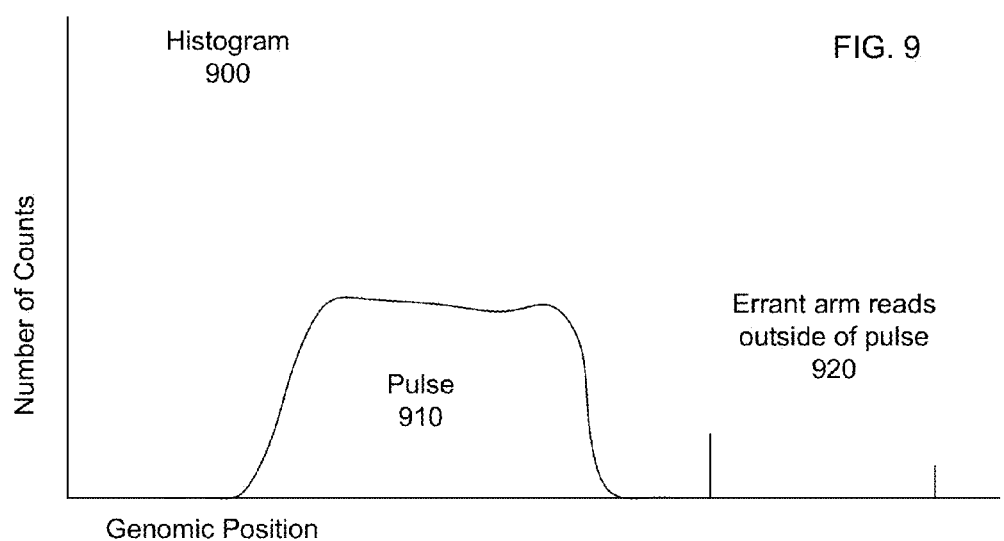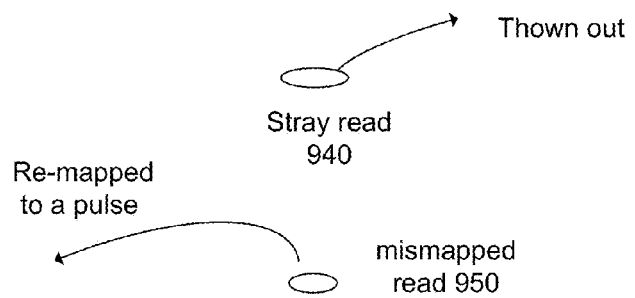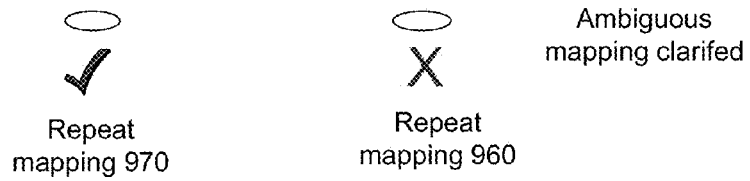
FIG. 9

Connectivity Matrix 1000

Het 2

|  | | a | c | g | t | o |
|---|---|---|---|---|---|---|
| Het 1 | a | 1 |  | 3 |  |  |
|  | c |  |  |  | 5 |  |
|  | g |  | 1 |  |  |  |
|  | t | 2 |  |  |  |  |
|  | o |  |  |  |  |  |

FIG. 10

Well 36

Well 53

Well 84

1610

Combined
Histogram
1630

| | | a | c | g | t | t | t | a | g | c |
|---|---|---|---|---|---|---|---|---|---|---|
| Reference Genome 2000 | | a | c | g | t | t | t | a | g | c |
| Assembled Diploid Genome 2010 | | a | c | n | t | a/t | n/t | | | |
| | | | | | | 2015 | 2017 | | | |
| Support Table 2020 | a | 10 | 0 | 0 | 0 | 7 | 3 | | | |
| | c | 0 | 9 | 0 | 0 | 0 | 1 | | | |
| | g | 0 | 0 | 5 | 0 | 1 | 1 | | | |
| | t | 0 | 0 | 0 | 12 | 6 | 7 | | | |
| Hap I Support Table 2030 | a | | | | | | 3 | | | |
| | c | | | | | | 1 | | | |
| | g | | | | | | 0 | | | |
| | t | | | | | | 0 | | | |
| Hap II Support Table 2040 | a | | | | | | 0 | | | |
| | c | | | | | | 0 | | | |
| | g | | | | | | 1 | | | |
| | t | | | | | | 7 | | | |

FIG. 20

IDENTIFICATION OF DNA FRAGMENTS AND STRUCTURAL VARIATIONS

CROSS-REFERENCE TO RELATED APPLICATIONS

The present application claims priority to and is a non-provisional of U.S. Provisional Patent Application 61/546,516 entitled "Detection And Identification Of DNA Structural Variations Using Log Fragment Read Methodology," by Kermani et al., filed Oct. 12, 2011, and U.S. Provisional Patent Application 61/623,876 entitled "Identification Of DNA Fragments And Structural Variations," by Kermani et al., filed Apr. 13, 2012, which are hereby incorporated by reference for all purposes.

FIELD OF INVENTION

Embodiments of the present invention are related to genomic sequencing, and more particularly to identifying long DNA fragments (e.g., using many short reads) and structural variations.

BACKGROUND

Genomic sequencing has progressed in the last few years. Methods can now sequence a sample within a relatively short time period (e.g., days) and with relatively small cost (less than $10,000). This reduced cost has opened up the possibility of using gene sequencing for diagnostic purposes, as well as more areas of research. To be suitable for diagnostic purposes, detailed information is needed, such as knowledge of the haploid genome (as opposed to just the diploid genome) and of structural variations.

Typical sequencing techniques simply provide information about the diploid genome, e.g., the genotype at many locations. However, for two heterozygous genomic locations, it is not known which haplotype (e.g., chromosome copy) that two alleles are on. The specific sequence of each of the two haplotypes can be critical information. However, short sequence data (e.g. 35 bp of each end of a short fragment) does not lend itself to easily identifying the haploid genome.

To make the identification of the haploid genome even more difficult, the genome of the sample currently being tested can have structural variations (e.g. insertions or deletions), which can also be of critical importance. Discovering structural a variation of a genome relative to a general or localized population can provide valuable diagnostic and research information. For example, structural variations typically are the result of disease, such as cancer, or can lead to a greater likelihood of cancer. Besides disease identification, accurate identification of structural variation can be important for many reasons, such as accurately tracking the heritage of a group of people, as the rearrangement might have occurred several generations previously.

In the last few years, structural rearrangements have emerged as an important driver of unchecked growth in many solid tumors. However, there are few easy to use, high-throughput methods for detecting these on a clinical scale. Current next generation sequencing (NGS) methods rely on paired end sequencing of relatively short reads (<200 bp) to detect structural rearrangements (SVs). While these methods have successfully detected some SVs, they perform poorly in regions of the genome containing repetitive elements, which are common hotspots of genomic rearrangements. Also, these mate-pair methods can be cumbersome, require high coverage, and also lose utility for long translocations.

The ideal method for detecting structural rearrangements would be a long single-molecule sequencing technology spanning the chromosome breakpoint usually involving long repeats and containing sufficient unique flanking sequence to allow for accurate mapping. Currently there are no commercial technologies that can achieve this on a scale and cost that is meaningful for genetic analysis in humans.

It is therefore desirable to provide methods, systems, and apparatuses that accurately identify long DNA fragments and structural variations in a genome.

BRIEF SUMMARY

Embodiments of the present invention can provide systems and methods for identifying long DNA fragments and structural variations. Various short reads can be grouped and identified as coming from a same long DNA fragment (e.g., by using wells with a relatively low-concentration of DNA). A histogram of the genomic coverage of a group of short reads can provide the edges of the corresponding long fragment (pulse). The knowledge of these pulses can provide an ability to determine the haploid genome and to identify structural variations.

According to one embodiment, a method detects a structural variation in a genome of a sample from an organism. Sequence data is received from a sequencing of a plurality of nucleic acid molecules of the sample. The sequence data includes sequences of at least one portion of each nucleic acid molecule. For each nucleic acid molecule, at least one sequence of the nucleic acid molecule is aligned to a reference genome. Each aligned sequence is associated with at least one other aligned sequence based on a presumption that the two sequences are potentially derived from a same fragment of DNA. Each of a plurality of histograms for a first chromosomal region can be calculated in the following manner. A respective group of sequences is identified as potentially being derived from a same fragment of DNA. The fragment includes at least a portion of the first chromosomal region. For each genomic position of a plurality of genomic positions within the first chromosomal region, a number of instances that an aligned sequence of the respective group includes the genomic position is aggregated. The histograms are compared to identify a common increase or decrease in the histograms within a same window of the first chromosomal region. The common increase or decrease is identified as a location of a structural variation in the first chromosomal region of the genome of the organism.

According to another embodiment, a method identifies DNA fragments from sequencing data of a sample of an organism. Sequence data is received from a sequencing of a plurality of nucleic acid molecules of the sample. The sequence data includes sequences of at least one portion of each nucleic acid molecule. For each nucleic acid molecule, at least one sequence of the nucleic acid molecule is aligned to a reference genome. Each aligned sequence is associated with at least one other aligned sequence based on a presumption that the two sequences are potentially derived from a same fragment of DNA. A histogram for a first chromosomal region can be calculated in the following manner. A first group of aligned sequences is identified as potentially being derived from a same fragment of DNA that includes at least a portion of the first chromosomal region. For each genomic position of a plurality of genomic positions within the first chromosomal region, a number of instances that an aligned sequence of the first group includes the genomic position is aggregated. A genomic location of a pulse in the histogram is determined. The genomic location of the pulse includes a beginning of the pulse and an end of the pulse. The sample is identified as having a first fragment of DNA that includes a sequence corresponding to the reference genome at the genomic location of the pulse.

Other embodiments are directed to systems and computer readable media associated with methods described herein.

A better understanding of the nature and advantages of the present invention may be gained with reference to the following detailed description and the accompanying drawings.

BRIEF DESCRIPTION OF THE DRAWINGS

FIG. 6A shows an approximate smearing effect to a pulse of a histogram. FIG. 6B shows a more realistic shape of the histogram by showing fluctuations within the histogram as modulated by the overall smearing effect. FIG. 6C shows an outline of a histogram 640 with one sharp edge and one smeared edge.

FIG. 9 shows examples of improvements in mapping using a location of a pulse of a well according to embodiments of the present invention.

FIG. 10 shows a connectivity matrix 1000 for a pair of hets according to embodiments of the present invention.

FIG. 20 shows a diagram illustrating an assembly process that can use the haplotype clusters of the pulses to resolve ambiguities in the basecalls of the haploid genome.

DEFINITIONS

Figure 1:
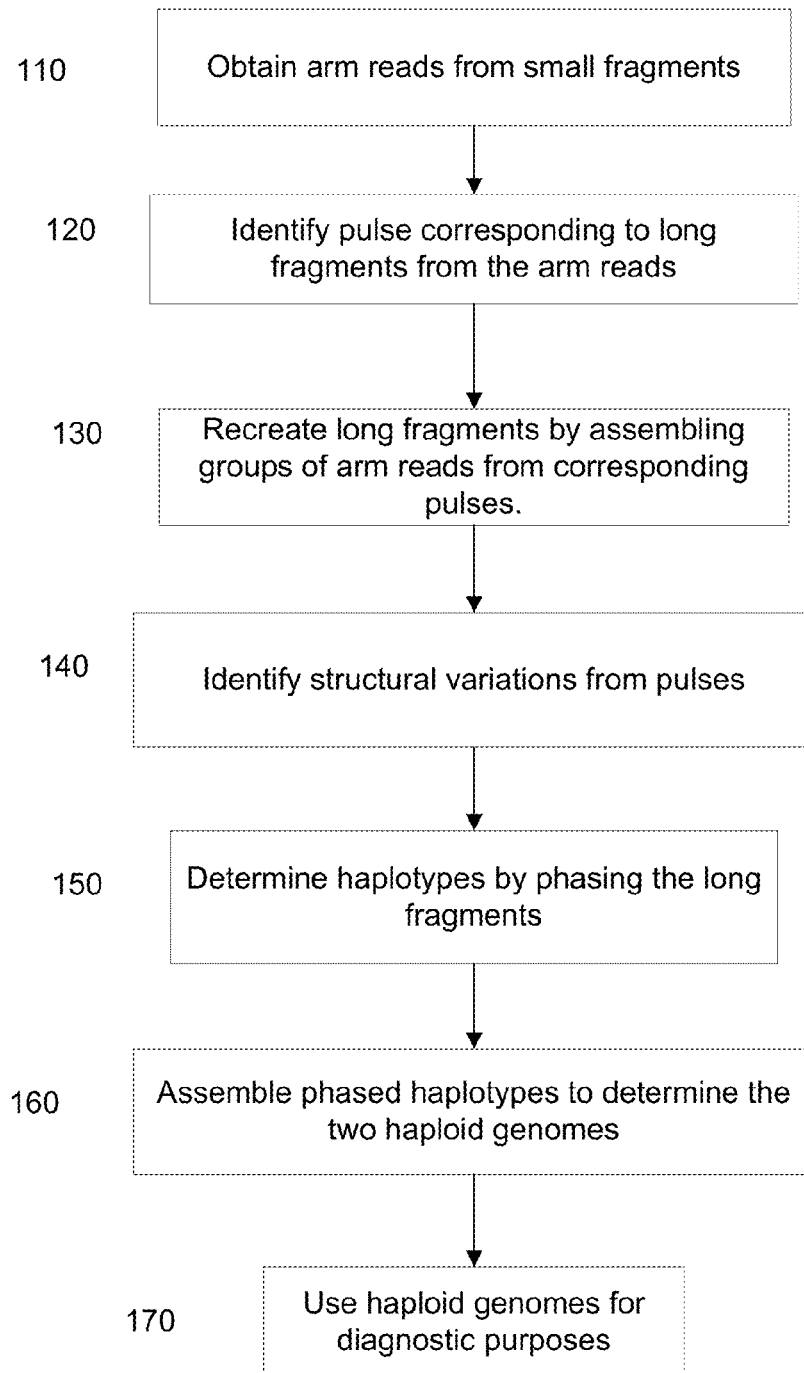
FIG. 1 is a flowchart illustrating a method 100 for determining the haploid genome of an organism according to embodiments of the present invention.

The following definitions may be helpful in providing background for an understanding of embodiments of the invention.

"Polynucleotide", "nucleic acid", "oligonucleotide", "oligo" or grammatical equivalents used herein refers generally to at least two nucleotides covalently linked together in a linear fashion. A nucleic acid generally will contain phosphodiester bonds, although in some cases nucleic acid analogs may be included that have alternative backbones such as phosphoramidite, phosphorodithioate, or methyl-phosphoroamidite linkages; or peptide nucleic acid backbones and linkages. Other analog nucleic acids include those with bicyclic structures including locked nucleic acids, positive backbones, non-ionic backbones and non-ribose backbones.

The term "reference polynucleotide sequence", or simply "reference", refers to a known sequence of nucleotides of a reference organism. The reference may be an entire genome sequence of a reference organism, a portion of a reference genome, a consensus sequence of many reference organisms, a compilation sequence based on different components of different organisms, a collection of genome sequences drawn from a population of organisms, or any other appropriate sequence. The reference may also include information regarding variations of the reference known to be found in a population of organisms. The reference organism may also be specific to the sample being sequenced, possibly a related individual or the same individual, separately drawn (possibly normal to complement cancer sequence).

"Sample polynucleotide sequence", or simply "sample sequence", refers to a nucleic acid sequence of a sample or target organism derived from a gene, a regulatory element, genomic DNA, cDNA, RNAs including mRNAs, rRNAs, siRNAs, miRNAs and the like and fragments thereof. A sample polynucleotide sequence may be a nucleic acid from a sample, or a secondary nucleic acid such as a product of an amplification reaction. For a sample polynucleotide sequence or a polynucleotide fragment to be "derived" from a sample polynucleotide (or any polynucleotide) can mean that the sample sequence/polynucleotide fragment is formed by physically, chemically, and/or enzymatically fragmenting a sample polynucleotide (or any other polynucleotide). To be "derived" from a polynucleotide may also mean that the fragment is the result of a replication or amplification of a particular subset of the nucleotide sequence of the source polynucleotide.

As used herein, a "fragment" refers to a nucleic acid molecule that is in a biological sample. Fragments can be referred to as long or short, e.g., fragments longer than 10 Kb (e.g. between 50 Kb and 100 Kb) can be referred to as long, and fragments shorter than 200 bases can be referred to as short. Embodiments can perform paired-end sequencing of fragments to obtain a left arm read and a right arm read for each fragment. Other embodiments can just perform a single arm read. As used herein, a "mate pair" or "mated reads" refers to the right arm and left are also called a mate pair. "Mapping" refers to a process which relates an arm read (or a pair of arm reads) to zero, one, or more locations in the reference to which the arm read is similar, e.g., by matching the instantiated arm read to one or more keys within an index corresponding to a location within a reference.

As used herein, an "allele" corresponds to one or more nucleotides (which may occur as a substitution or an insertion) or a deletion of one or more nucleotides. A "locus" corresponds to a location in a genome. For example, a locus can be a single base or a sequential series of bases. The term "genomic position" can refer to a particular nucleotide position in a genome or a contiguous block of nucleotide positions.

The molecules "of a sample" can also include clones that result from amplification of the molecules. A molecule can be derived from a fragment in several ways. For example, a fragment could break into smaller parts (molecules), with each part being part being derived from the fragment. Additionally, any clones resulting from amplification or replication of the parts can be considered as being derived from the fragment.

A "histogram" is any determination of an aggregation of sequences that include each of a plurality of locations. A histogram does not need to be displayed. A histogram may be a count of the original sequence reads or result from a processing (e.g., filtering) of the raw data, e.g., a density plot made by a low-pass filtering of counts for genomic regions (e.g., 1 kb bins). As used herein, "base coverage" refers to a count of the number of sequence reads at a particular genomic position. As used herein, "clone coverage" is computed from two arm reads of a same fragment (e.g., a small fragment whose ends are sequenced) and the bases that exist between the two arm reads. The clone coverage can be determined from aligning the two arm reads, and then counting the base coverage of the two arm reads and incrementing a count for each of the genomic positions in the mate gap. The term "genomic coverage" includes base coverage and clone coverage.

As used herein, "Well ID" refers to a bar code or tag that is added to a small fragment to determine which well the arm read comes from. Small fragments with a same well ID can be used to reassemble a long fragment. Two chromosomal regions can be considered "proximal" to each other when a physical fragment of DNA includes at least a portion of each region.

A "structural variation" refers to a variation in a sample genome from a reference genome, where the variation is on the order of 1 kb to 3 kb, or larger. Examples include copy-number variations (such as deletions and amplifications), inversions, translocations, and insertions, all of which can be intra-chromosomal and inter-chromosomal, and may involve novel sequences. A "break" refers to an identification of a location where a structural variation exists. As explained herein, a break can be determined from well-specific histograms that share a common increase/decrease. A break may be identified by just either the sequence to the left or the right of the break. A "junction" refers to the break along with an identification of the two sequences that join at the break.

DETAILED DESCRIPTION

As described above, it can be difficult to obtain detailed information about the haploid genome of a diploid organism from a biological sample of the organism, at least at a commercially viable cost and speed. For example, short sequence reads provide low cost, but are difficult to assemble into a haploid genome (i.e. the two respective haplotypes of the diploid genome). Embodiments can identify a group of short sequence reads that are from a same long fragment (e.g., part of a same pulse), e.g., by denoting which well the short read is from. The genomic location of a group of short reads can be used to identify the location of the long fragment (e.g. using a histogram of genomic coverage). The pulse can be filled in with the short sequence reads to obtain at least a partial sequence of the long fragment. These long fragments can then be used to determine the haploid genome in a more efficient manner than by using the short sequence reads directly.

Additionally, these pulses (or at least one edge of a pulse) can be used in a process which allows detection of the structural variations (e.g., intra-chromosomal and inter-chromosomal translocations and inversion). Embodiments can leverage the length of the long fragments to find a common break in the long fragments. The common breaks can then be paired to determine junctions of the regions that are translocated. The translocations that are targeted can include most of the real-life types of translocations, i.e., segments that are significantly larger than the mate-pair distance, and therefore cannot successfully be identified with mate-pair information. Other translocations can be identified with mate-pair information.

I. Overview

FIG. 1 is a flowchart illustrating a method 100 for determining the haploid genome of an organism according to embodiments of the present invention. Method 100 can be performed using sequencing data from a biological sample of the organism. For example, cells may be obtained from the organism, and the DNA in the cells can be sequenced. In one implementation, the DNA is put into multiple wells as long fragments, and then broken into small fragments, as will be described in a later section.

In step 110, arm reads are obtained from small fragments. In one embodiment, one arm read for a small DNA fragment may be obtained. In another embodiment, both ends of a small fragment can be sequenced to obtain mated arm reads (e.g. of about 35 bases). These mated arm reads can be aligned to a reference genome to estimate the position of the corresponding small fragment in the sample genome. The positions of the various small fragments can be tracked to determine the long fragments, which were broken up to obtain the small fragments.

In step 120, pulses corresponding to long fragments can be identified based on the arm reads. For example, the arm reads from a particular well (aliquot) will concentrate on certain regions corresponding to the long DNA fragments that were present in the well. This concentration of the reads in certain (fragment) regions, followed by unpopulated regions is used to identify pulses. In one aspect, a pulse can be seen in a histogram of counts of the arms reads for positions in the genome. These pulses, in turn, approximate the actual fragments that caused the concentration of the reads into certain regions. In one aspect, the amount of long fragments in a well is kept relatively small (e.g., 0.1× of the genome) so that the likelihood of two fragments being close or overlapping is small.

In step 130, the long fragments are recreated (at least partially) by assembling groups of arm reads from corresponding pulses. For example, the pulses can be identified from the high concentration of arm reads in a histogram. The sequences of the arm reads that formed a particular pulse can then provide bits and pieces of the sequence of the corresponding long fragment. Accordingly, the long fragments can be identified per well, and therefore, haploid calls can be made. This can simplify the subsequent processing steps, and result in higher accuracy, given a lower sequencing coverage.

In step 140, structural variations can be identified from the pulses. For example, assume that the sample genome includes an insertion of part of chromosome (Chr) 9 in Chr 7. In that case, any long fragments that span this junction will result in a pulse that ends at the junction, which will be described in more detail later. For example, multiple pulses on Chr 7 will be seen to end at or near the junction, and multiple pulses on Chr 9 will be seen to start at or near the junction. These two breaks can be paired (correlated) to identify the junction in the sample genome where the part of Chr 9 was inserted in Chr 7. The correlation can use the number of wells where both of the breaks show up.

In step 150, the two haplotypes are determined by phasing the long fragments. The long fragments can be clustered into two groups that are each internally consistent (or at least substantially consistent) with each other. Such clustering can use single nucleotide polymorphisms (SNPs) to identify long fragments that have the same allele at a particular locus, and perhaps other common alleles. These long fragments could form the start of a cluster, and other long fragments can be added to find overlapping, consistent long fragments.

In step 160, the phased haplotypes can be assembled to determine the two haplotype genomes. The sequence data of all of the arm reads of a first haplotype (i.e. cluster of long fragments) can be combined to provide a first haploid genome, and the sequences of the arm reads for the second haplotype can be combined to provide the second genome. The structural variations determined in step 140 can also provide information for the assembly. For example, the haploid genome can properly reflect an insertion of part of Chr 9 into Chr 7.

In step 170, the haploid genome can be used for diagnostic purposes. For example, the location and nature of the structural variations could be used to identify diseases, e.g., when the cells are taken from a tumor. The haplotype structure can also be used to identify predisposition to certain diseases or whether a patient might respond to certain therapies.

The numbering of the steps does not signify an order. For example, one can perform step 140 after some or all of the phasing in step 150 before step 140. Thus, the process can be iterative such that the method can revert back to earlier steps for another pass through the steps. Any of the methods described herein can also be iterative and/or performed in a different order where suitable.

II. Identifying Pulses

The identification of pulses was discussed above for step 120 of method 100. A pulse in a histogram of the genomic coverage of arm reads was identified as corresponding to a long fragment originally in the sample. The long fragments were at last partially re-created in a cost-effective manner using the arm reads, thereby enabling cost-effective techniques for investigating the haploid genome. The following discussion provides additional details of embodiments that identify a pulse from sequencing data.

Figure 2:
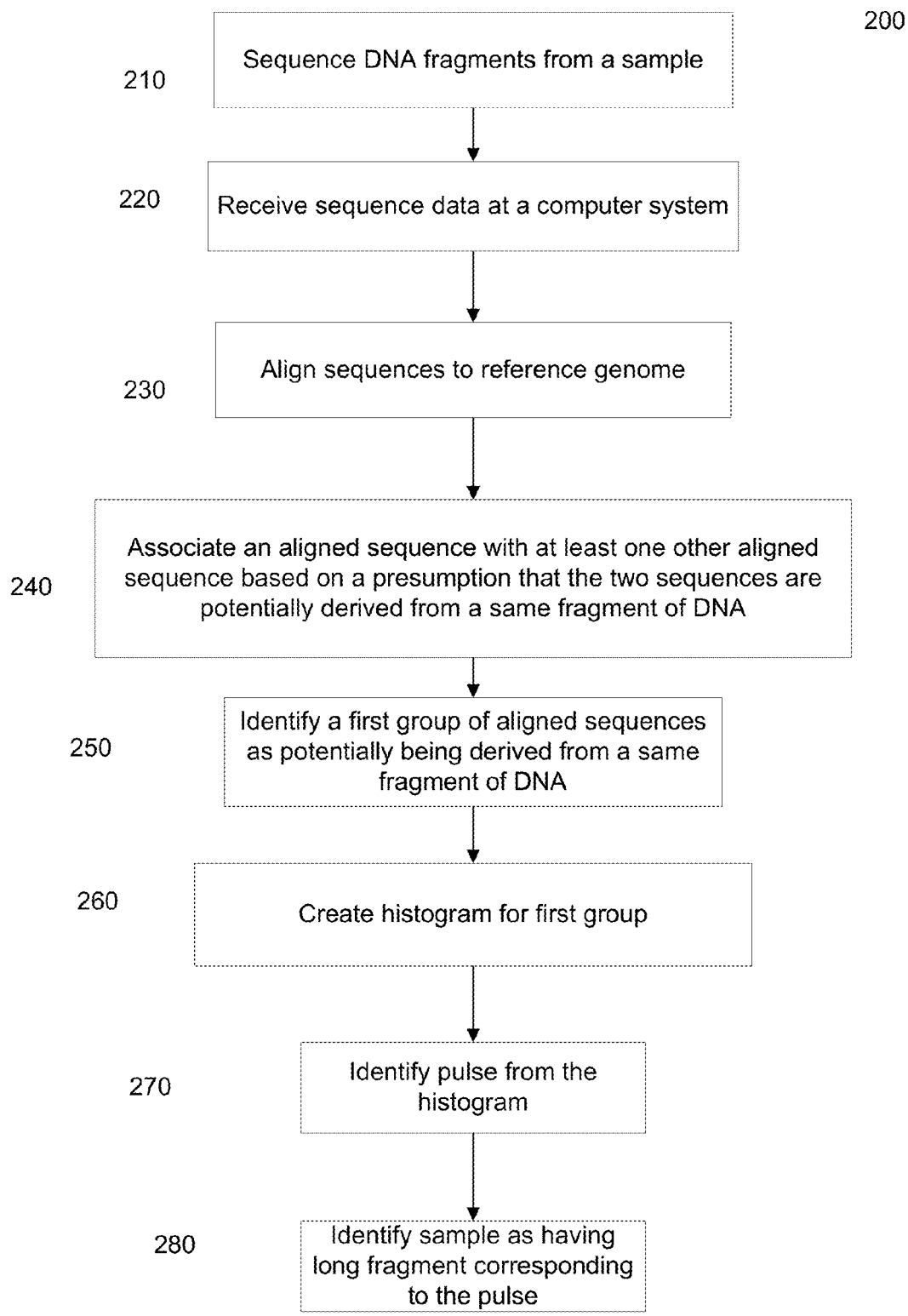
FIG. 2 is a flowchart illustrating a method 200 of identifying DNA fragments from sequencing data of a sample of an organism.

FIG. 2 is a flowchart illustrating a method 200 of identifying DNA fragments from sequencing data of a sample of an organism. All or parts of method 200 can be performed to accomplish step 120 of method 100. Method 200 can provide an identification of a long fragment of DNA in the sample and sequencing data for at least some of the genomic locations within the long fragment.

In step 210, DNA fragments from a sample are sequenced. The sample may be separated into various wells before sequencing, where each well contains a relatively low percentage (e.g. 10%) of the genome. At this point, the well may contain long fragments, which may be broken up into small fragments. These short fragments can be barcoded to keep track of which well they came from. Various types of sequencing techniques may be used, e.g., as described in U.S. application Ser. No. 12/816,365 entitled "Methods and Compositions for Long Fragment Read Sequencing" by Drmanac et al.

In step 220, sequence data from a sequencing of a plurality of nucleic acid molecules of the sample is received. The sequence data includes sequences of at least one portion of each nucleic acid molecule. These sequences can be the mated arm reads of the small fragments, which may be obtained in step 210.

In step 230, at least one sequence of each nucleic acid molecule is aligned to a reference genome. In an embodiment where both arms are sequenced, the mated reads can be aligned together to provide greater accuracy of alignment and to obtain a location of the entire small fragment (although only the sequence data for the arm reads is obtained, and not the sequence of the mate gap). In one aspect, the arm reads can map together to the top strand or bottom strand (complementary to top).

In step 240, each aligned sequence is associated with at least one other aligned sequence based on a presumption that the two sequences are derived from a same long fragment of DNA. The presumption can be based on the fact that both sequences were obtained from a same well. If two sequences are known to be obtained from a same small fragment (e.g. from a same read or from a pair of mated reads), such knowledge can determine that the two sequences were obtained from a same fragment.

In various embodiments, data can be used to determine if two aligned sequences (e.g., two alleles) are derived from a same fragment. If the two alleles are considered to be on the same fragment, then that data point would suggest that the two alleles are on a same haplotype. In one embodiment, the two alleles being on the respective arm reads of a mate pair is used to indicate that the two alleles are on the same fragment, and thus the same haplotype, but such information may provide few data points. In another embodiment, an inference can be made that two alleles were on an original larger fragment that had since been broken up into smaller fragments, which are then sequenced wholly or partially (e.g. paired-end sequencing). In one implementation, the inference can be made using long fragment read (LFR) techniques as described in U.S. Pat. No. 7,709,197, entitled "Nucleic Acid Analysis By Random Mixtures Of Non-Overlapping Fragments" filed Jun. 13, 2006, and U.S. patent application Ser. No. 12/816,365, entitled "Methods And Compositions For Long Fragment Read Sequencing" filed Jun. 15, 2010, the contents of which is incorporated by reference.

Such techniques can be combined. For example, the arm reads of a same fragment can be used, as well as LFR techniques that use arm reads for any fragment of a same aliquot. In one embodiment, arm reads of a same fragment could be given a higher weight than when the arm reads are from different fragments (but from a same aliquot).

In step 250, a first group of sequences are identified as potentially being derived from a same long fragment of DNA. The sequences may be identified as being from a same long fragment when the sequences were obtained from a same well, e.g., as determined by a barcode that acts as a well ID. The first group of sequences may be derived from many long fragments (e.g., all of the long fragments originally in a same well); but since each sequence is part of the first group, each sequence is effectively identified as potentially being from a same long fragment.

In step 260, the computer system calculates a histogram for the first chromosomal region. At least some of the sequences are from the first chromosomal regions, and thus at least one of the long fragments includes at least a portion of the first chromosomal region. To create the histogram, a number of instances that an aligned sequence of the first group includes a genomic position in the first chromosomal region is aggregated. For example, a counter for a particular nucleotide position in the genome (or a bin of 1 kb long) can be incremented for each aligned sequence. When paired-end sequencing is used, the genomic positions of the mate gap can also be incremented (corresponding to clone coverage), as is described below.

In one embodiment, to overcome computer memory limitations, the data stream with mapping and group information from steps 230 and 250 is compressed for transmission to a another device of a system (which may be networked or stand-alone devices). Also, both the data stream of mapping information and grouping (e.g. by well) and the coverage data can be labeled and stored by chromosome and well ID number (i.e., {chromosome #, well ID #}).

In step 270, a pulse is identified in the histogram. The genomic location of a pulse can be determined in a histogram. The genomic location of the pulse includes a beginning of the pulse and an end of the pulse. Various techniques may be used to determine a pulse so that it likely corresponds to an actual long fragment, and not to noisy data. For example, a region where the histogram is above a threshold value can be identified, and such sub-pulses that are near each other can be combined. As another example, functions (which may be derived from actual data) can be used to expand the histogram to fill in gaps of the histogram, as well as determine edges of the pulses.

In step 280, the sample is identified as having a first long fragment of DNA that includes a sequence corresponding to the reference genome at the genomic location of the pulse. The identification can be made because the pulse reflects the short sequence reads that were obtained from the first long fragment. Once the short sequence reads are collected as a group, counted in a histogram, and identified as a pulse, the pulse can be used to determine the length, genomic location, and composition (e.g., partial sequence data) of the corresponding long fragment. The first long fragment could be longer than the pulse, e.g., when the first long fragment includes a structural variation. In that case, the first long fragment would be combination of two or more pulses, depending on the number of junctions that the long fragments covers.

III. Sequencing Using Well Number

As mentioned above, the well that a particular arm read of a fragment is obtained can be tracked. This well ID can be determined using a barcode that is attached to a small fragment. Thus, the origin of the small fragments can be tracked. The following describes various implementations, which may, for example, be used for steps 210-240.

Figure 3:
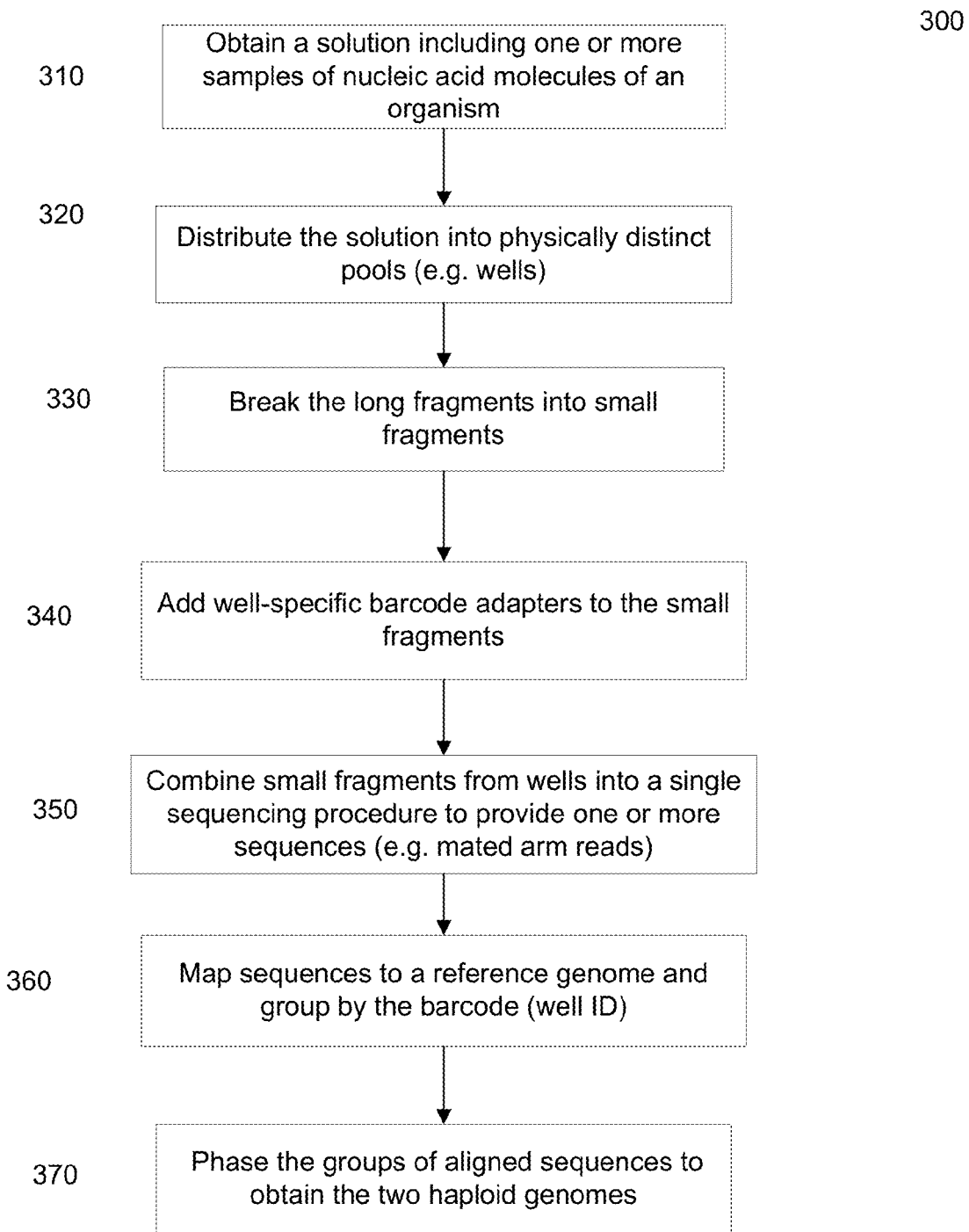
FIG. 3 is a flowchart illustrating a method 300 for obtaining short sequence reads for assembling into long fragments according to embodiments of the present invention.

FIG. 3 is a flowchart illustrating a method 300 for obtaining short sequence reads for assembling into long fragments according to embodiments of the present invention. Method 300 will be described in conjunction with FIG. 4, which shows a diagram illustrating steps of method 300.

Figure 4:
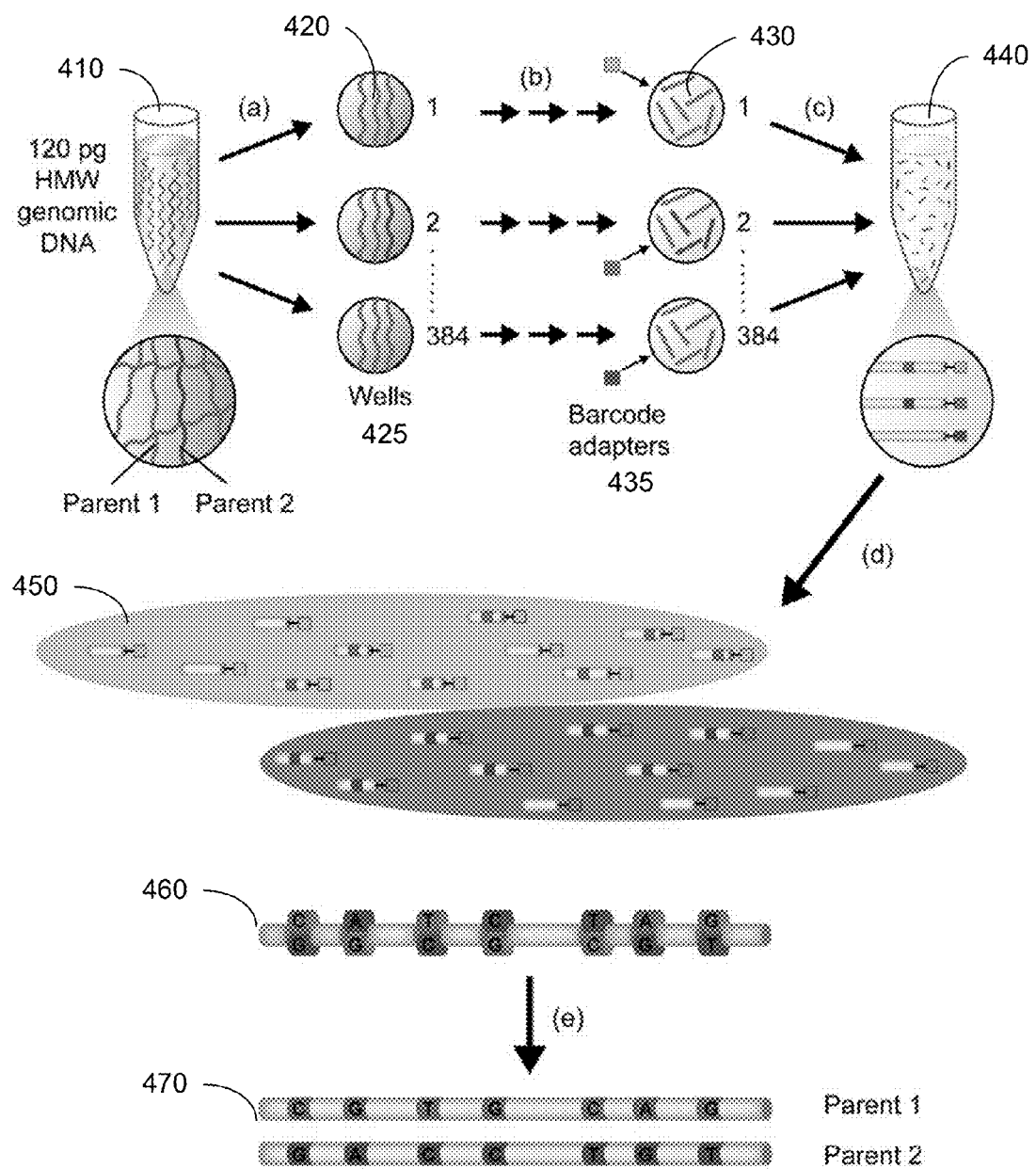
FIG. 4 shows a diagram illustrating steps of method 300.

In step 310, a solution including one or more samples of nucleic acid molecules of an organism is obtained. Note that a sample can be a solution. The solution can be created from tissue samples, or samples obtained from a bodily fluid. As shown in FIG. 4, sample 410 has approximately 120 pg of high molecular weight DNA. The DNA inherited from each parent is highlighted in blue (parent 1) and red (parent 2). In the solution, the nucleic acid molecules tend to be much longer than after the solution is dispensed (e.g. from a pipette) as an aliquot into wells for preparation for sequencing. These very long fragments in the sample 410 can be about 100 kb to 1 mb in length.

In step 320, the solution is distributed into physically distinct pools (e.g. wells). FIG. 4 shows in (a) the DNA being physically separated into 384 distinct wells 420. The separation can be a stochastic separation of corresponding parental DNA fragments into the physically distinct pools. The act of dispensing typically breaks up the nucleic acid molecules, e.g., as they move through the tip of the pipette. The nucleic acid molecules before dispensing are termed very long fragments, and the nucleic acid molecules after dispensing are termed long fragments. The long fragments in a well (or other container holding a single aliquot) are about 5 Kb to 50 Kb in length (or up to a few 100s of Kb).

In one embodiment, the solution 410 can be relatively diluted with respect to the DNA (e.g. as few as about 10 to 30 cells may be in the solution). This dilution can provide an aliquot containing around 10% of the genome when the solution is dispensed from a pipette. As the fraction of the genome in each pool decreases to less than a haploid genome, the statistical likelihood of having a corresponding fragment from both parental chromosomes in the same pool decreases. For example, at 0.1 genome equivalents per well, there is a ten percent chance that two fragments will overlap and a fifty percent chance those fragments will be derived from separate parental chromosomes; yielding a five percent overall chance that a particular well will be uninformative for a given fragment. Thus, given that the long fragments are randomly distributed throughout the solution, the original fragments of an aliquot are not likely to be from overlapping regions of the genome, nor be close to each other, and to be from different copies of a chromosome.

These long fragments can be amplified (cloned). For example, a highly uniform amplification using a modified phi29-based multiple displacement amplification (MDA) (Dean, F. B. et al. 2002, PNAS Vol. 99, pp. 5261-6) was performed to increase the number of each long fragment of DNA to 5,000-10,000 copies per well. Amplification can help to provide better statistical data for the histograms. The long fragments are not be cloned at all, or may be cloned in later steps.

In step 330, the long fragments are broken into small fragments. FIG. 4. shows the long fragments 425 being broken into small fragments 430 as shown in (b). The long fragments can be fragmented, e.g. using enzymatic fragmentation, multiple displacement amplification (MDA) with random primers, and/or physically fragmented (e.g. using sonic fragmentation). Short fragments result from the fragmentation of the long fragments. As part of an enzymatic process or as an additional step, the resulting short fragments may be amplified. In various embodiments, the resulting short fragments can be about 100-10,000 bases, or a more narrow range of 200 bases to 5,000 bases, and may be 500 bases on average.

As part of the fragmentation into small fragments, the long DNA molecules can be processed to blunt ended 300-1,500 bp fragments through controlled random enzymatic fragmenting (CoRE). CoRE fragments DNA through removal of uridine bases, incorporated at a predefined frequency during MDA, by uracil DNA glycosylase and endonuclease IV. Nick translation from the resulting single-base gaps with E. coli polymerase 1 can resolve the fragments and generate blunt ends.

In step 340, well-specific barcode adapters are added to the small fragments. Thus, the short fragments of a single aliquot can be coded, as described in U.S. patent application Ser. No. 12/816,365, to track the short fragments from a same well, when the short fragments from all wells are pooled into a single sequencing procedure. FIG. 4 shows barcode adapters 435 being added to the small fragments 430. Each well has a barcode that is unique to that well. In one embodiment, unique 10-base error correcting barcode adapters, designed to reduce any bias caused by differences in the sequence and concentration of each barcode, are ligated to the fragmented DNA in each well using a high yield, low chimera formation protocol (Drmanac, R. et al. 2010, Science, Vol. 327, pp. 78-81). In one implementation in step (b), all within the same well without intervening purifications, the genomic DNA is amplified, fragmented, and ligated to unique barcode adapters.

In step 350, the small fragments from the wells are combined into a single sequencing procedure to provide one or more sequences (e.g. mated arm reads). In FIG. 4 at (c), the fragments from all 384 wells are combined into a single vessel 440, with the barcode adapters 435 distinguishing the origin of each small fragment. Any sequencing platform can be used to obtain an entire sequence of a small fragment, one arm read, or a pair of mated reads. In one embodiment, an unsaturated polymerase chain reaction using primers common to the ligated adapters can be employed to generate sufficient template for sequencing (Drmanac, R. et al. 2010, Science, Vol. 327, pp. 78-81). The small fragments can also be purified before the sequencing process begins. Alternatively, one could sequence each well in a separate process, but this can be time consuming.

The more individual pools interrogated the greater number of times a fragment from the maternal and paternal complements will be analyzed in separate pools. For example, a 384 well plate with 0.1 genome equivalents in each well results in a theoretical 19× coverage of both the maternal and paternal alleles.

In step 360, the sequences are mapped (aligned) to a reference genome and grouped by the barcode (i.e. by well ID). FIG. 4 shows group 450 of the sequences obtained from fragments from well 1, while he other group is of sequences obtained from fragments from well 2. A histogram can be determined from the genomic coverage of each group. The pulses can be determined from non-zero or relatively high regions of the histograms (such regions may be contiguous or nearly contiguous with small gaps). As each group corresponds to long fragments that are likely not to be overlapping, the pulses can be determined to correspond to the long fragments 420. Accordingly, certain embodiments can track the aliquot (or well) from which a sequenced fragment was obtained, thereby recapturing information about the longer fragments that existed in the solution. This information about the longer fragments can provide more information about the respective chromosomes.

For example, when a low concentration sample is used, if arm reads from any two fragments in a same aliquot (well) are close in genomic location (as determined from the mapping), it can be assumed that they originated from a same original long fragment in the solution. Thus, the arm reads do not have to be of a same small fragment, but can be from any two fragments that are from the same aliquot. Such tracking provides more information about large regions on the chromosomes.

In step 370, the groups of aligned sequences can be phased (e.g. using the pulses) to obtain the two haploid genomes. Since pulses represent the boundaries of the long fragments, and each long fragment in sub-genome aliquoting such as LFR represents (with >95% confidence) a haploid genome, such a process can significantly simplify the task of DNA assembly. Ultimately, a high coverage complete sequence of both maternal and paternal chromosomes can be generated. FIG. 4 shows a diploid genome 460 of heterozygous loci that is phased into the two haploid genomes 470 with the help of the knowledge of the long fragments. In the case of cancers, complex structural rearrangements can be correctly identified with increased sensitivity and without location bias, as will be described later for structural variations.

IV. Creating Histograms

As mentioned above, embodiments can create histograms (e.g. in step 260) corresponding to the sequence data obtained from sequencing all or portion(s) of the small fragments of a particular well or multiple wells (i.e. the genomic coverage from multiple wells can be summed together to create a single histogram). In one embodiment using paired-end sequencing of the small fragments, the mated reads are mapped to a reference genome. As mated reads are mapped, a tally matrix can be updated or created after all mappings are done.

In various embodiments, a tally matrix can contain the following columns: A, C, G, and T, along with any one or more of N, X and L. These letters identify the counts of A/C/G/T/N/X/L, respectively, for a base at a specific position (row of the matrix) of interest. The number of rows can correspond to the number of bases in the reference genome. The columns for A, C, G, and T are for base calls corresponding to the appropriate base.

N and X refer to the soft no-calls and hard no-calls, respectively for the base at the specific position. A soft no-call is a basecall that had a score below a certain threshold (e.g., 0.1), and therefore was changed (later on during the process) to no-call. A hard no-call is a basecall that was not made, due to registration failure, etc. If a position has non-zero values for A/C/G/T/N/X, then that position would have a non-zero values for a histogram using base coverage.

L marks the clone coverage for each mated pair. The clone coverage corresponds to the base positions in the mate gap between the two mapped arm reads of a mated pair, in addition to the base positions corresponding to the arm reads themselves. Further details on mate pairs can be found in U.S. patent application Ser. No. 13/016,824, which is incorporated by reference. For the specific positions within the mate gap, the L column is incremented. L can also be incremented for the positions of the arm reads. For example, if the mated reads (including the mate gap) spans a 770 base wing, all of these 770 positions could have their L values incremented (or equivalently just the mate gap can have L incremented, with clone coverage being a combination or the L values and base coverage). A tally matrix can be created for each well or for multiple matrices, just as the matrices can.

A. Base Coverage

Figure 5A:
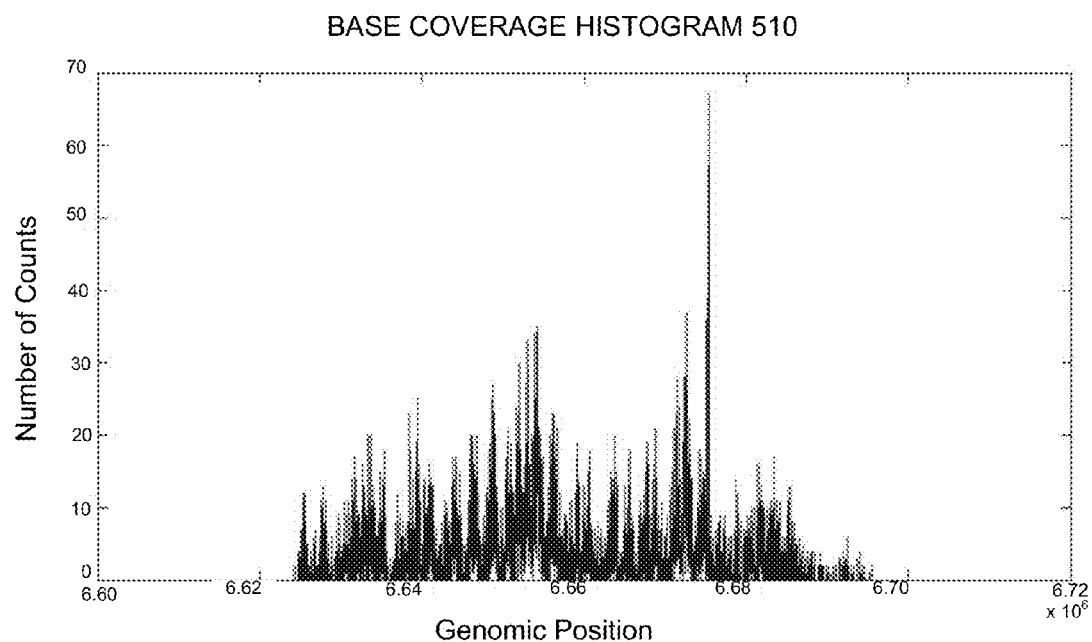
FIG. 5A shows a histogram 510 using the base coverage of a well.

FIG. 5A shows a histogram 510 using the base coverage of a well. The horizontal axis corresponds to a genomic position. As shown, the horizontal axis spans a length of 120 Kb. The vertical axis is the number of counts of specific positions where an arm read had a base call that was mapped to that position (even if it was an N). Histogram 510 and other histograms can be created from the tally matrix, other data structure, or directly from the sequencing data without first being counted in another data structure.

As shown, the base coverage is from the arm reads of a single well. The arm reads could map to a top strand or bottom strand of the reference genome at a particular location. Note that a specific position of the reference genome can have multiple bases to indicate a SNP. Thus, one cell sequenced with 1× coverage would be expected to have four counts contribute to the histogram, one for each strand of each chromosome copy. Thus, the histogram can track a number of times a particular location in the genome has a sequenced tag (arm read) aligned to that location.

Based on histogram, one can identify a pulse that starts around 6.625 and ends around 6.695. This pulse roughly corresponds to a long fragment that was in the well from which the histogram was created. That is, the arm reads of histogram 510 are from a same long fragment that was fragmented further into small fragments, whose arm reads were aligned to the reference genome to create histogram 510.

If the sequencing coverage is high, the base coverage histogram can show genomic regions of high coverage separated by regions of low coverage (e.g. zero or near zero). However, high sequencing coverage costs more. Without high sequencing coverage, finding a contiguous region to identify the boundaries of each long fragment (within that well) would be difficult. Thus, in some implementations, the base coverage may not be suitable for the identification of the pulses, as the per-well base coverage is very low (0.1×). Using clone coverage can alleviate this problem.

B. Clone Coverage

Figure 5B:
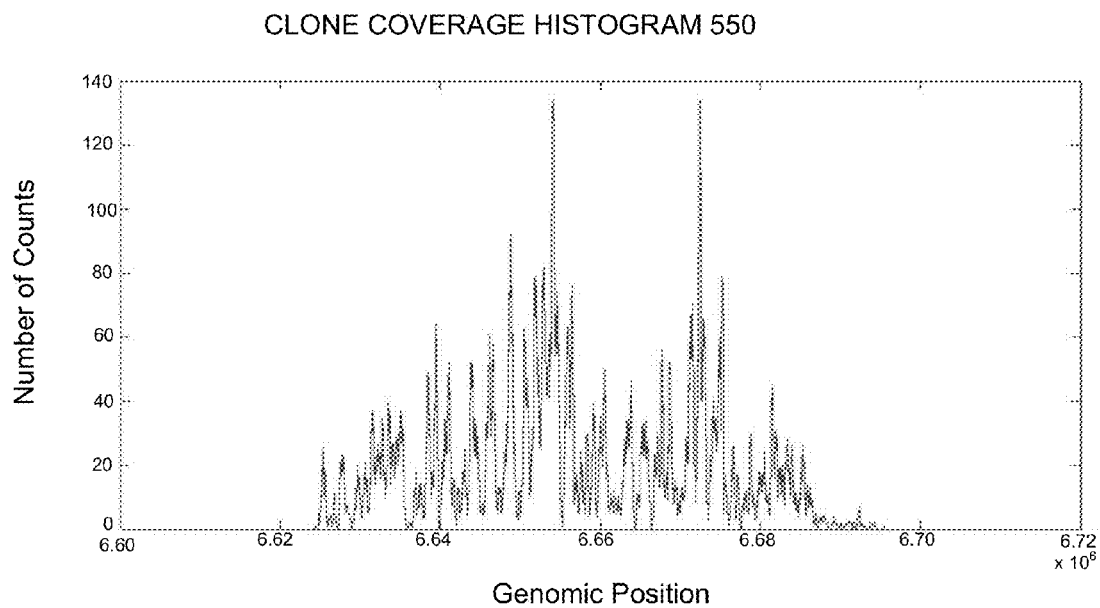
FIG. 5B shows a histogram 550 using the clone coverage of a well.

FIG. 5B shows a histogram 550 using the clone coverage of a well. The horizontal axis is the same as in FIG. 5A, but the Y axis now corresponds to counts for clone coverage, which will result in more positions having a non-zero value and having a greater Y value, as can be seen in the scale being twice that of FIG. 5A. As mentioned above, the clone count can be included in the tally matrices. A clone count is 1 if the mated reads of a small fragment or its mate gap fall in that position, and is 0 otherwise. For each sequence of a small fragment that contributes to this feature, a counter is incremented for that specific position. At the end of mapping, the counter shows the clone coverage for that position on the genome.

Accordingly, using clone coverage for a histogram assumes anything in the mate gap exists, and adds one to the histogram. Since the mate gap is long compared to the arm reads, which leads to greater heights in the histogram (e.g., non-zero instead of zero), a computer system can more easily identify the pulse. The coverage of the L is estimated to be approximately 7 to 10 times the base coverage, i.e., the sum of the base (A/C/G/T/N/X) coverage, due to the large size of the mate gap. Ratio=(base size of mated arm reads+ length of all the gaps)/(mated arm read size)~(70+400 to 600)/70=(480 to 680)/70=(6.86 to 9.71).

C. Relation to Pulse

A purpose of a histogram is to identify a pulse in the counts of a histogram, where the pulse corresponds to a long fragment in the well. For example, a pulse can be used to estimate the genomic location of the long fragment. The histograms may have values much larger than one (e.g. an average of 10-20 with maximums from 200 to one or two thousand) when amplification of the short fragments is performed.

A histogram from a single fragment can be considered a pulse in that the genomic coverage is zero before the fragment and zero after the fragment. As mentioned above, even though the base coverage is 0.1×, the clone coverage would be 7 to 10 times of that, i.e., 0.7× to 1.0×. For simplicity of the arguments, assume the clone coverage is approximated at 1×. In that case a plot of clone coverage on the genome (for one well) would ideally show a 1× coverage where the long fragments are and 0× elsewhere. However, there can be issues, such as the sporadic noise (mis-mapping), the disjunction of the sub-regions of a fragment within the 1× coverage; and identification of edges when pulse slowly tapers at an end. The disjunction of sub-regions can at least partially be addressed by averaging techniques.

D. Averaging

Even using clone coverage, a histogram can have relatively small regions of low counts between regions of high counts, due to the statistical nature of the sequencing process. In other words, there are areas with 0× coverage, and there are areas with >1× coverage. The data shows that areas of up to 10 times the expected average can exist. Therefore, there are areas that will have a coverage between 1× and 10×, and areas with 0× coverage.

Embodiments can fill in or otherwise account for such intersperse low count regions in various ways. For example, a fragment has 1× coverage on average. In order to increase the evidence, and to fill the remaining internal gaps, one could use the fact that the genomic coverage is not uniform. As part of such a process, the system can perform a binning to create the histogram. As mentioned above, the horizontal axis can be a bin of 1 kb (or of some other suitable length), where the bin count is an aggregate of the counts for positions within that bin.

Typical sizes of bins are around 1000 or 2000 bases; typical frequency is $\frac{1}{1000}$ or $\frac{1}{2000}$ correspondingly. As an illustration, in case of a bin being 1000 bases and frequency 1 bin per 1000 bases, the method can take the first 1000 elements of the clone coverage array (histogram), average them, and write element 1 of the averaged array (histogram). Then, the next 1000 bases—to element 2 of averaged array, etc. The resulting length is 1000 times smaller than the length of input array of the entire genome. In the above example, bins come one after another without gaps or overlapping. In this case, when bin size is N, the frequency is simply 1/N. However, to analyze bins with smaller shift and to make them overlapped, a greater frequency can be used. Such overlapping bins effectively provides a moving average.

Besides a moving average, a more complex density function can be applied in order to average out these differences. These density functions can have their own fuzzifying functions, which could be rectangular, trapezoidal, bell-shaped, etc. A purpose of using a density function at this point is to leverage the variation in the mapping coverage within one fragment of a well, thereby making it even. For example if the coverage ranges from 0× to 2×, by using this function, the system may get an average of 1× coverage. This 1× coverage will cover the holes that may arise at any point in the process.

V. Pulse Detection

As mentioned above, a histogram for a particular well can be used to identify a long fragment, whose sequence is helpful in determining the haploid genome of the organism. This section describes various techniques, which may be used in combination, to detect a pulse. The detection of a pulse can include just the determination of one edge of the pulse, both edges, and can include determining at least a portion of the sequence of the corresponding long fragment. These techniques can be used for step 270 of method 200.

Effectively, the pulse detection is re-creating the long fragment from the short fragment reads, as it is assumed that the short fragments of a same well are from a same long fragment (at least as long as the short fragments overlap or are relatively close). One problem that can is exist are gaps in a region that cannot be sequenced. Another problem can be to differentiate between two pulses of a well corresponding to two long fragments (non-overlapping) that are close to each other (where both could be from a different haplotype), or actually corresponding to just one long fragment (which would be from one haplotype) composed of the two pulses.

A. Removing Random Noise

As an initial step, random mapping noise may be filtered by requiring a minimum coverage per base (i.e. genomic base position) per well. In one implementation, a typical absolute minimum coverage is two mappings for the same position. In another implementation, a minimum coverage would not be used, e.g., when no amplification is performed on the short fragments. Such an initial filter would not correspond to the detection of a pulse, and can be done before any averaging (e.g., binning).

B. Determining Coverage Above a Height Threshold

A pulse can be detected at a coarse level, with potential refinements later (but such refinements are not required), or just detected at a refined level. The coarse level can use the averaging techniques to create an averaged histogram described above in order to perform the coarse level analysis. For example, for each well, the clone coverage data may be averaged by user-selected bins with adjustable size and frequency, as was described above. Such a coarse level histogram can then be analyzed to determine a pulse, and then a histogram without binning (although a smoothing density function can be used) may be analyzed to determine edges of a pulse more accurately. This coarse level analysis can also eliminate some noise signal as well. In other embodiments, just the raw clone coverage without any averaging (raw histogram) may be used.

To identify a location of a long fragment as having been in a specific well (as signified by a pulse), a program running on a computer can scan the averaged clone coverage (or raw clone coverage) for the individual well and record the continuous areas above a detection threshold. The detection threshold can be either defined by user based on DNA sample characteristics, or calculated based on actual clone coverage distribution or un-averaged (raw) on a per well basis or summed over all wells (or even an average per well as determined from all wells). In one embodiment, the program can discard detected pulses that are too short (which may be considered as useless or unreliable detection).

In one embodiment, a threshold for using with an averaged histogram or raw histogram can be calculated for each well individually. For example, a two-step process can include: 1) determine global median over all wells and exclude all data (raw or averaged) below the global median; 2) for a particular well, calculate a well average by values that are not excluded and use 50% of the well average as the threshold. Either step may be used by itself as well.

Once a continuous area of the averaged histogram is found to be above a threshold, that continuous area can be considered to be from a same fragment. Due to the statistical nature of the sequence and the amount of sequencing coverage, a long fragment could result in multiple continuous areas that separated. Thus, at this point, one can consider a continuous area to be a sub-fragment, where multiple sub-fragments can be combined.

C. Combining Sub-Fragments

After determining the sub-fragments of a well, embodiments can then determine whether any two sub-fragments should be combined. As mentioned above, with a 1× apparent coverage, there would be disjoint regions corresponding to each long fragment. These are the areas that arm reads did not have a good coverage.

Embodiments can look at the proximity of two pulses to combine them (which may be limited to procedures when no amplification is performed). For example, a distance threshold (such as 0-4 Kb) can be used to determine whether combine two pulses. The distance threshold can simply be applied to the edges of the pulses, but can also be applied to the underlying data, which could account for the actual counts at or near the edges of the pulses. Thus, the system can simply join any two fragments if they are within a specified distance. The method can also look at the number short pulses in an area (e.g., a density or frequency) to identify the short pulses that can be combined to represent a single long fragment. In other embodiments, the system can discard pulses that are too short, e.g., as being useless or unreliable detection.

Before or instead of using a distance threshold, a morphological dilation function can operate on the histogram, such that the sub-fragments are expanded. Since the morphological dilation expands the sub-fragments, the result can be a combination. As part of this joining of the sub-fragments, morphological dilation and morphological erosion can be used. The sub-fragments corresponding to each fragment can be joined together by the morphological dilation function. Due to dilation, the boundaries will grow beyond the original values, and sub-fragments that touch may be combined into a new larger sub-fragment (which could be the final long fragment). The dilation can operate on any histogram, e.g., one using raw data or average data in bins.

After this joining process, the original edges of a new larger sub-fragment can be recovered. In order to bring the boundaries back to where they were, a morphological erosion function is used. This function shrinks the boundaries, except if two areas have joined already, it would not be able to make them disjoint again. The combination of dilation followed by erosion is referred to as morphological closing operation.

These morphological operations can use a kernel that defines the extent of the operations. The size of the kernel should be matched to the expected size of the gaps one tries to fill. Too small kernel sizes result in some gaps to remain disjoint. Too large kernel sizes result in some spurious noise to join the fragments, and therefore extend the fragments beyond their real boundaries. Therefore, care should be taken in using the optimal kernel size. The kernel size can be estimated on-the-fly from the data. For example, a functional experiment can be done on a region. For instance, a random or a guided search can be done on different kernel variables. Then, the outcomes of each setting can be compared to the expected values (based on the known inputs, e.g., number of cells). As the quality of mapping improves, larger kernels can be used without any penalties. In one implementation, a theoretical bound for the kernel size is the minimum separation between two fragments in a well, which can be determined for the concentration of DNA in the sample.

D. Determination of an Edge of a Pulse

Depending on the desired accuracy, the edge of the pulse (corresponding to the long fragment) can be determined as the edge of the sub-fragments as determined from the averaged histogram, after the combining. Thus, in one embodiment, the edge is simply the end of the bin that is above a threshold, where no bins within a certain range are also above the threshold. For greater accuracy, the system can analyze the raw histogram in the neighborhood of the last bin (for either edge) that was identified as being above a threshold. The analysis of this bin can then refine the edge with greater resolution than the bin size. Thus, the positions of the long fragment's (pulse's) start and end can be further refined by considering un-averaged (raw) clone coverage data (both total and per well). For example, the (raw data can be analyzed to better identify a point where the raw clone coverage becomes large enough that a start of the pulse (associated with a long fragment) can be identified.

Once the relevant section of the raw histogram is determined, the drop in the counts at the edge can be analyzed. Various techniques can be used to analyze this section of the raw histogram. For example, a location that the counts dip and stay below an edge threshold could be used. The edge threshold could be the same, or at least related, as the height threshold used previously to determine the sub-fragments (depending on whether and how the bin count was normalized). In one embodiment, the edge threshold could be a certain percentage of the previous threshold (e.g., after conversion to the appropriate value for the raw histogram).

As other examples, the threshold can be based on the raw coverage of that specific well or the raw coverage of all of the wells, or certain subgroup. Also, the threshold can be an absolute value (e.g., 5 or 10), or relative values (such as 30% of average for the pulse or 30% of maximum value). Another example for a threshold include 50% of global average coverage per genome divided by number of biological cells used in the experiment. In other embodiments, a median point between the location that the histogram hits a higher (e.g. near the height threshold) and a lower threshold (e.g., near zero), or a slope (rate of change) of the decrease can be used to identify the edge.

Filtering to Determine Edges of Pulses

The techniques described above may have problems when the edge is not well-defined. For example, often the edges will be smeared (a slow decrease), and thus not be a well-defined edge. This can be due to variations in the amplification of parts of the long fragment to create the small fragments, to which paired-end sequencing is performed (e.g. due to MDA). For example, the ends of a long fragment are not amplified as much as the middle of a long fragment. Even for other fragmentation methods, the small fragments can lose bases at the end of the small fragment before sequencing, and for small fragments from the ends, this can result in a smearing. Or, very small fragments for the end will result, and these will not be sequenced.

FIG. 6A shows an approximate smearing effect to a pulse of a histogram. The horizontal axis is genomic position. The location of the long fragment corresponding to a pulse is shown as 610. Due to smearing at the ends, the resulting histogram tapers off slowly at the ends, which makes identification of the actual edges of the fragment very difficult. The overall smearing effect is shown as a functional curve 620, which can act as a modulation to the counts that are actually measured.

FIG. 6B shows a more realistic shape of the histogram by showing fluctuations within the histogram as modulated by the overall smearing effect. Histogram 630 shows an actual histogram given a smearing effect resulting from the sequencing procedure. Histogram 630 is created by averaging per 1000-base window. Histogram 630 has relatively small peaks and valleys that may be due to variations in sequencing coverage, but the overall shape is modulated by the smearing effect 635 so that histogram 630 begins to taper off before the edge of the long fragment is actually encountered. The variations in histogram 630 can also be due to different primers hybridizing to different sections in non-uniform manner for MDA. Thus, the actual small fragments may follow a more complicated process that can move above or below an average. Thus, the count at any one location can have contextual dependencies (local variation).

FIG. 6C shows an outline of a histogram 640 with one sharp edge 642 and one smeared edge 644, as outlined with the contour 645. The sharp left edge 642 may result from a structural variation occurring at that edge. For example, if the long fragment was did not end at that edge, but had a novel insertion at the edge, then the histogram would still show an edge. Structural variations are discussed in more detail later.

To calculate an accurate location of an edge, when smearing exists, embodiments can use an inverse transform to make the smeared end of the pulse in the histogram to be sharp. The transform can be a function that takes a sharp edge (e.g., a step function) to be smeared. For example, a transform (Fourier transform or a convolution) of a step function can be used to smooth out the step function, and the inverse transform can be used to generate an approximate step function of the smeared end. For example, a convolution can be defined that receives a step function as an input, and whose output is similar to the tail of a pulse of real data. The parameters of a suitable convolution (e.g., the function for the convolution) can be optimized to provide a best approximation to the actual data seen. As part of a functional optimization, a series of random or guided transform function variables can be used, and under each condition the statistics of the pulses can be provided. The system can select the best option as the one with statistics that match the histogram of the sample or an expected histogram (e.g., based on known physical values form other samples).

Figure 7A:
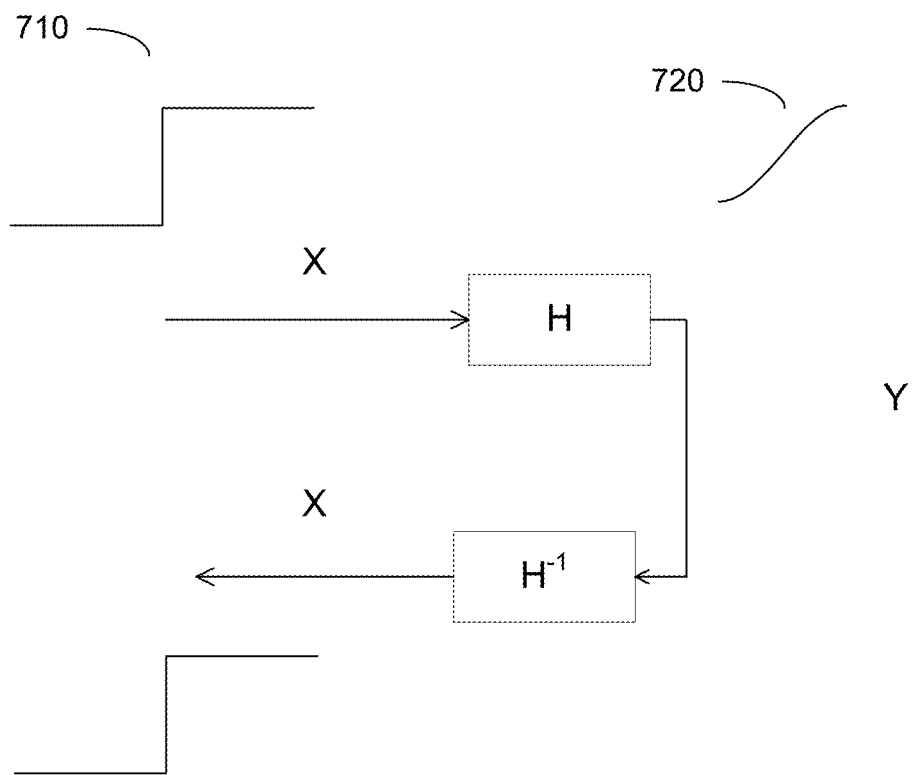
FIG. 7A shows a diagram involving the operation of a transform H on a step function to provide a smeared function and the operation of an inverse transform $H^{-1}$ to regain the step function.

FIG. 7A shows a diagram involving the operation of a transform H on a step function to provide a smeared function and the operation of an inverse transform $H^{-1}$ to regain the step function. The step function 710 is denoted as the input X to the transform H. The output Y of the transform H is a smeared edge 720. For example, an approximation of the step function with just a few Fourier functions (e.g. sine or cosine) would result in a smear edge 720. If Y was fed into the inverse of transfer H (denoted as $H^{-1}$), then the step function 710 is retrieved. The transforms can be created so as not to shift a location of the edges.

In one embodiment, H is calibrated using smeared edges of an actual histogram data. For example, if a smeared edge is known to exist, then an H that produces an output Y that has a similar shape to the smeared edge can be used. The parameters of the transform H (e.g., linear and non-linear coefficients and the type of basis functions of the transform) can be varied until the output best fits the shape of the actual data. Equivalently, the real data could then be compared to various classes of Y, and the closest Y is chosen, where each Y has a corresponding transform H. Various embodiments can have a different H (and thus $H^{-1}$) for each sample, or each lane for each sample. For example, the H can be determined to match the tailing ends of well histograms from that lane or sample. Thus, the transform H can account for the contextual dependencies as mentioned for FIG. 6B.

Figure 7B:
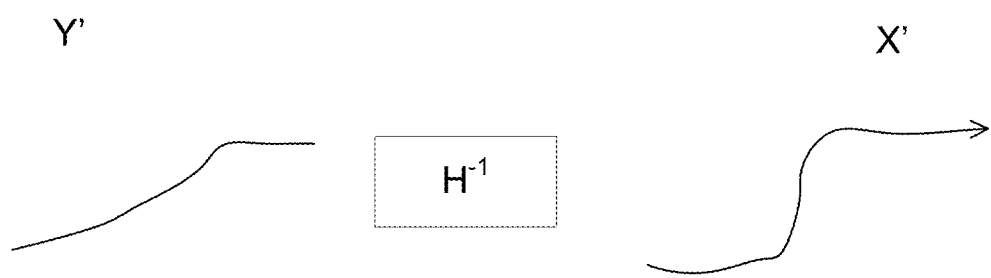
FIG. 7B shows the operation of the inverse transform $H^{-1}$ on a smoothed edge of a pulse to obtain a relatively sharp edge of a pulse.

FIG. 7B shows the operation of the inverse transform $H^{-1}$ on a smoothed edge of a pulse to obtain a relatively sharp edge of a pulse. Once the transform H is determined, an inverse $H^{-1}$ of the transform can be calculated. The inverse $H^{-1}$ can then operate on the actual data to output a function that approximates the step function. Once an approximate step function is obtained, the location of the edge can be determined, e.g., the median distance between two threshold values or other techniques described herein.

Identifying Only One Edge

For some applications, only one edge of a pulse may need to be identified. For example, for structural variations only one edge of a pulse is needed to identify a break, which can then be used to identify a junction. As described later, the edges of some pulses may align as a result of a structural variations (e.g. an insertion or deletion). In such a case, the edges may be synchronized to find an approximate region that the junction of the variation exists. Since the natural end of a fragment may show up as a smeared edge while a sharp edge may more likely result from a structural variation, a sharp edge (e.g., as measured by a slope of the histogram or drop over a specified distance) can be used to identify a structural variation, as shown in FIG. 6C.

E. Sequence of Pulse

Once the edges of a pulse are identified, the arm reads that map to the reference genome between the two edges can be used to at least partially determine the sequence of the long fragment corresponding to the pulse. In one instance, this step can be considered a type of assembly.

For example, within each long fragment, the basecalls (for the 1× average coverage) can be combined. When the coverage is 1×, the "assembly" may simply repeat the information from the small fragments that mapped to that area. If the 1× coverage is for clone coverage, in reality the result is 0.1× of the bases called with bases and 0.9× of them filled with Ns. But, it is important to note is that the system can now provide pulses that contain all the basecalls that were made for that pulse/well combination.

In one embodiment, for each location within a pulse at which a read occurred, there is at least one base call. For locations that are in the clone coverage (gap), these would just have an N (but were counted for determining edges of pulse). Locations that were between sub-fragments that were combined, these locations also would have an N. If a location has multiple reads, where the base call differs among the reads, the base in the majority can initially be determined as the base at that location. These base calls can be modified as described below.

For each base call of an arm read, the probability of the top base call, each base call, or some subset can be saved and used in an initial determination of the base or for corrections. For example, the probabilities for calling a base at a same location of multiple reads (potentially from a same well or other wells) can be combined, instead of just counting one for each majority base call of an arm reads. In this manner, an overall probability of each base call across arm reads can be used to determine the base at the location. In one embodiment, the total of the probabilities for the two top bases for a pulse can then be saved for error correction below.

F. Method

Figure 8:
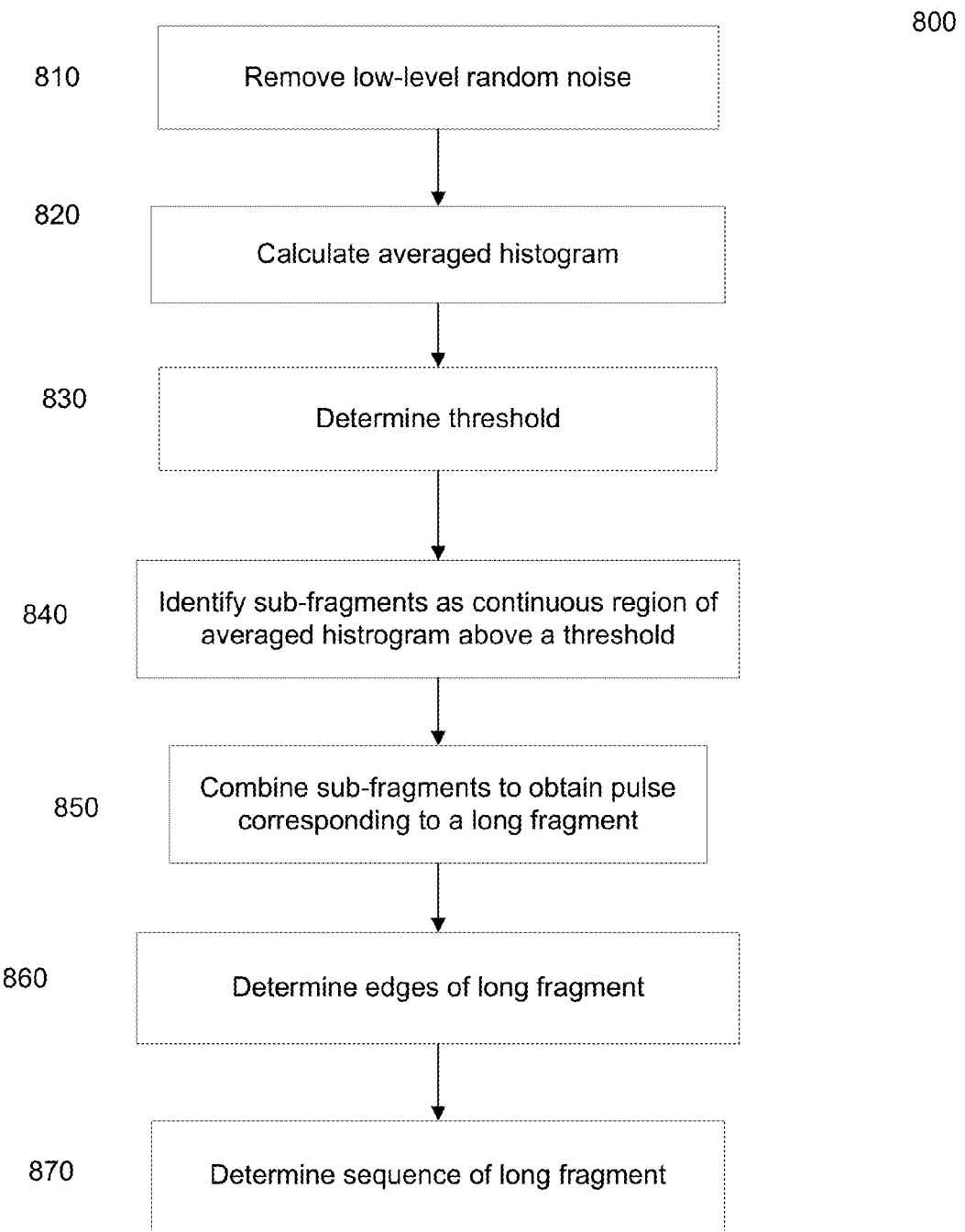
FIG. 8 is a flowchart of a method 800 for detecting a pulse according to embodiments of the present invention.

FIG. 8 is a flowchart of a method 800 for detecting a pulse according to embodiments of the present invention. As with other methods, certain steps are optional and the order can be rearranged where possible. Method 800 can use base coverage or clone coverage of counts from a well.

In step 810, low-level noise is removed, for example as described above. The level for removing the noise can depend on the amount sequencing performed. In step 820, an averaged histogram is calculated. As described above, the averaging can involve binning the counts, a moving average, or more complex density function.

In step 830, a threshold is determined (e.g. computed) for use in a following step. The threshold can be determined from the actual coverage obtained, using various options, such as a percentage of coverage, as detailed above. In step 840, contiguous regions of the averaged histogram above the threshold are identified as sub-fragments. In step 850, certain sub-fragments can be combined based on a proximity of the sub-fragments (which can use dilation function). The combined sub-fragments compose a pulse that can be correlated to a long fragment, or part of a long fragment if a structural variation exists.

In step 860, the edges of the long fragment are determined. The edges can simply be the locations where the pulse falls below a threshold. In more complex techniques, the raw histogram at the level of base resolution is analyzed to determine a more accurate determination of an edge. In step 870, the arm reads are combined to at least partially determine the sequence of the corresponding long fragment.

VI. Improving Pulses

Once a pulse is identified, the location of the pulses for a particular well can be used to improve the underlying data used to identify the pulse. For example, since the system knows where long fragments are (by pulses) for a particular well, if mate reads map to a location far from the pulses, the system can identify that there is an error, such as (1) the mapping can be incorrect or ambiguous; (2) there is an error in the barcode tag, and thus the fragment may actually be from a different well; and (3) the arm reads are incorrect due to errors in the base calls.

A. Improving Mapping

With knowledge of where the long fragments from a well fit into the reference genome, the system knows where the arm reads from that well should be located, and thus where they should not be located. If an arm read maps to an area that is outside of the boundaries of the pulses of a well, then that arm read may be mismapped. Besides identifying mismapped arm reads, the pulses of a well can help in correcting the mapping. With the size of the possibly mapping being restricted to the locations of the pulses, the mapping of an errant arm read can be easier. If an arm read cannot be accurately mapped to this smaller area of the reference genome (i.e. the regions of the pulses), then the mismapped arm read could be removed from further analysis.

Additionally, many arm reads are discarded due to multiple mapping. These arm reads can be resurrected with the additional knowledge of the regions where the arm read should and should not map. Since the pulses are a small portion of the genome, it is highly likely that areas that normally have multiple hits on the genome, have only one hit for the pulses identified for a particular well. Therefore, these arm reads can be properly identified.

Once the proper mapping are used, the properties of the pulse can be re-computed. For example, with additional data points being added to the histogram, the pulse edges could change and the newly mapped data could fill in gaps within the pulse (e.g. where no actual reads had been identified, which could provide variations from the reference genome).

FIG. 9 shows examples of improvements in mapping using a location of a pulse of a well according to embodiments of the present invention. Histogram 900 shows a location of a pulse 910 and errant arm reads 920 that fall outside of any pulse in the well (note that other pulses of the well are not shown). The corresponding long fragment 930 is shown below histogram 900 and extends from the start to the end of pulse 910. Since errant arm reads 920 do not correspond to any long fragment, they may result from a mismapping.

In some cases, the arm read may simply be from a very small fragment that was originally in the sample. Stray read 940 is such an example. Since stray read 940 does not fall within a long fragment, the system can see of the read maps to any genomic positions of the pulses identified for the well. If the read does not map to a pulse, then the read can be identified as being a result of an error or just a very small fragment of DNA, which may not be very useful for further analysis. Accordingly, stray read 940 can be thrown out from further analysis. Such identification and removal of bad data can improve accuracy for any analysis using arm reads.

Mismapped read 950 is shown as being originally mapped to a location outside of pulse 910. However, once the pulses are identified, a second pass of the mapping procedure can be performed. As shown, this second pass re-maps the read 950 into pulse 910. Such an example could arise from errors in the original base calls of the arm read, which could make the original mapping location a slightly better match for alignment. If the mapping to pulse 910 is sufficiently close (e.g., only one or two mismatches), then the read may be re-mapped.

Problems also occur when a read is equally mapped to two locations. For example, arm reads that include a repeat sequence of the genome can cause ambiguity in alignment. Repeats are problematic since they can cause errors. An arm read is shown as mapping to both locations 960 and 970. If a sequence is mapped to multiple locations, one could (1) throws the data away (so only use uniquely mapped mate pairs); (2) select one of the aligned locations randomly; (3) or carries both forward with equal probability to handle later on (which is carrying forward noise). Embodiments can thus avoid such problems by identifying areas where a fragment should map, therefore effectively reducing the size of the genome that any one particular mate pair is mapped to (e.g. reducing by 10% if a well has 0.1x). As shown, repeat mapping location 960 is rejected and repeat mapping location 970 is accepted as the mapping location of the arm read, which could be one of a pair of arm reads.

B. Barcode Error

It is possible that an arm read that is far away form any pulse of a well could be because of an error in the bar code. Thus, besides the above mapping problems, an incorrect barcode could result in an arm read being considered as falling outside of a pulse. In other words, an arm read not being part of a pulse could be because of an error in reading the barcode. If such an arm read is identified, the proper bar code could be found. In this manner, the sequencing and mapping of the bar code can be corrected, e.g., if the base calls were actually similar and the probability of mapping to a different well is significant probability.

Additionally, often the well ID (barcode) of an arm read cannot be determined (e.g. 10% or 20% of the arm reads may fall in this category). These arm reads can be stored as well 0. These arm reads can still be mapped to the genome. If one or more of these arm reads falls within a pulse, the data for the arm read can be used to determine the sequence of the pulse and/or to readjust the edges. For example, in some cases, the barcode of the arm read could only be partially read. Thus, the well ID is not sufficient to determine the well, but when combined with the pulse information of a well that has a consistent barcode (i.e. is not severely different than the measured barcode), the read could be assigned to that well.

C. Error Correction for Pulses

The sequences of the pulses can be improved via the correction mentioned above, since additional arm reads could be added to a pulse. Additionally, the sequence information of the arm reads of a pulse can be corrected via a phasing procedure. For example, the basecalls from different arm reads could conflict with each other. Such inconsistencies can be identified within a well or for arm reads from different wells for pulses that cover a same region. Such identified inconsistencies and correction can provide more accurate reconstructed long fragments for later phasing and assembly.

In one embodiment, corrections can be performed by analyzing the base calls of arm reads that cover two specific heterozygous loci (e.g., SNPs). Each read corresponds to one of the two haplotypes. Therefore, the set of candidate reads at the position of the pair of heterozygous loci (hets) should belong to two major clusters, one corresponding to each parental chromosome. These reads of the two hets can be organized into a connectivity matrix. For instance, from the 40 reads that may fall on two specific het locations, 25 could belong to one cluster (one parental chromosome), 10 to the other cluster (the other parental chromosome), and 5 could be contributed by noise (false mapping, false basecalling, etc.). In such an example, some of the 5 errant basecalls could be changed (e.g., if the probability for the likely correct basecall is high enough), or be thrown out so as to not to cause problems with further analysis.

FIG. 10 shows a connectivity matrix 1000 for a pair of hets according to embodiments of the present invention. The rows correspond to the basecalls for Het 1 and the columns correspond to the basecalls for Het 2. The matrix elements correspond to the number of arm reads having the corresponding pair of base calls. The value O is for other basecalls, such as N or X. Note that the rows and columns could correspond to other alleles than single base calls. The connectivity matrix could show only two non-zero matrix elements that are not in a same two or column, as then there would be an inconsistency (or effectively one position would not be a het). In such a case, the identification of two clusters would be easy, as all of the data is consistent.

As one can see, connectivity matrix 1000 shows conflicting information for what the two haplotypes of this pair of hets could be. For example, there is strong data (5 counts) that one of the haplotypes has C at Het 1 and T at Het 2. But, the other haplotypes could have AG (3 counts) or TA (2 counts), or perhaps one of the others with 1 count. Various techniques can be sued to identify the cluster. The connectivity matrix can be determined using the arm reads across wells or the base calls of just one well.

In one implementation, once there are enough reads that match one of the two templates of interest, the corresponding reads can be declared mapped to one of the two possible haplotypes. If there are not enough reads or as a separate technique, the system can look at the number of counts for a particular row to determine if the counts can be merged. For example, one can look at matrix element AA having one count. If the corresponding arm read had G as the second highest probability basecall on Het 2 (the probability might still be subject to criteria to ensure it is sufficiently high), then the count can be moved to matrix element AG. This type of clustering of looking at a row or column effectively uses a distance element since those matrix element involve only the change of one basecall.

In this manner, one can determine the correct het values for each cluster. Thus, one can throw out pulses with incorrect data, suppress just parts of them that have incorrect data, or selectively change the base calls on a pulse to conform with a cluster. In one embodiment, only when the errors are clear are the errors corrected. There may be times when an error is not determine with sufficient accuracy. In such cases, the inconsistency may be carried forward to be cleared up later (e.g. during a phasing of the pulses).

Multiple connectivity matrices can be analyzed for a pulse. For example, the system could start with one pair of hets, establish the two clusters, and move to the next het, and repeat the process with one het of the first pair. The connectivity matrices can be analyzed in isolation of each other, or in combination. For instance, inconsistencies can be identified between the clusters (haplotypes) suggested by the connectivity matrixes of three different pairs of hets (e.g., Hets 1,2; Hets 1,3, and Hets 2,3).

Inconsistencies among arm reads in a well could be the result of the collision of two wells. For example, if two long fragments in a well overlap at least in part, and thus cover a same genomic region. The identification of two clusters could then help to identify such a collision and to resolve arm reads to different haplotypes, thereby breaking up what appears to be one long pulse into two pulses.

VII. LSV Method

Detection of genomic structural rearrangements (e.g. due to cancer) by next generation sequencing technologies (NGS) is currently limited by the read length and mate-pair gap length of the platform used. The typical NGS read length is 35-200 base pairs with a mate pair gap of 200-2000 base pairs, which can make translocations difficult to detect. To overcome such a limitation, embodiments can analyze the pulses in the histograms of the wells, or analyze the histograms directly. Pulses that share a common trait (e.g. start or end at a same location) can signify a variation, namely a break. If two breaks are correlated, then a junction can be identified (i.e., the sequence on other side can be determined). Since the pulses correspond to a long fragment, long translocations can be identified. Embodiments can enable the discovery of the real-life translocations, which are longer than the ordinary mate-pair distance in current technologies.

A. Variations

Some embodiments can determining a genome when a variation exists relative to a reference genome. For example, the variation can be an insertion of chromosome 9 (Chr 9) into chromosome 7 (Chr 7). In such a case, a variation can be identified for at least two regions, i.e., a break on chromosome 7 at the point where Chr 9 is inserted and a break at Chr 9 at the start of the inserted region. The two breaks can be correlated with each other to determine that they exist on the same strand of DNA, which allows that DNA strand to be determined.

Figure 11:
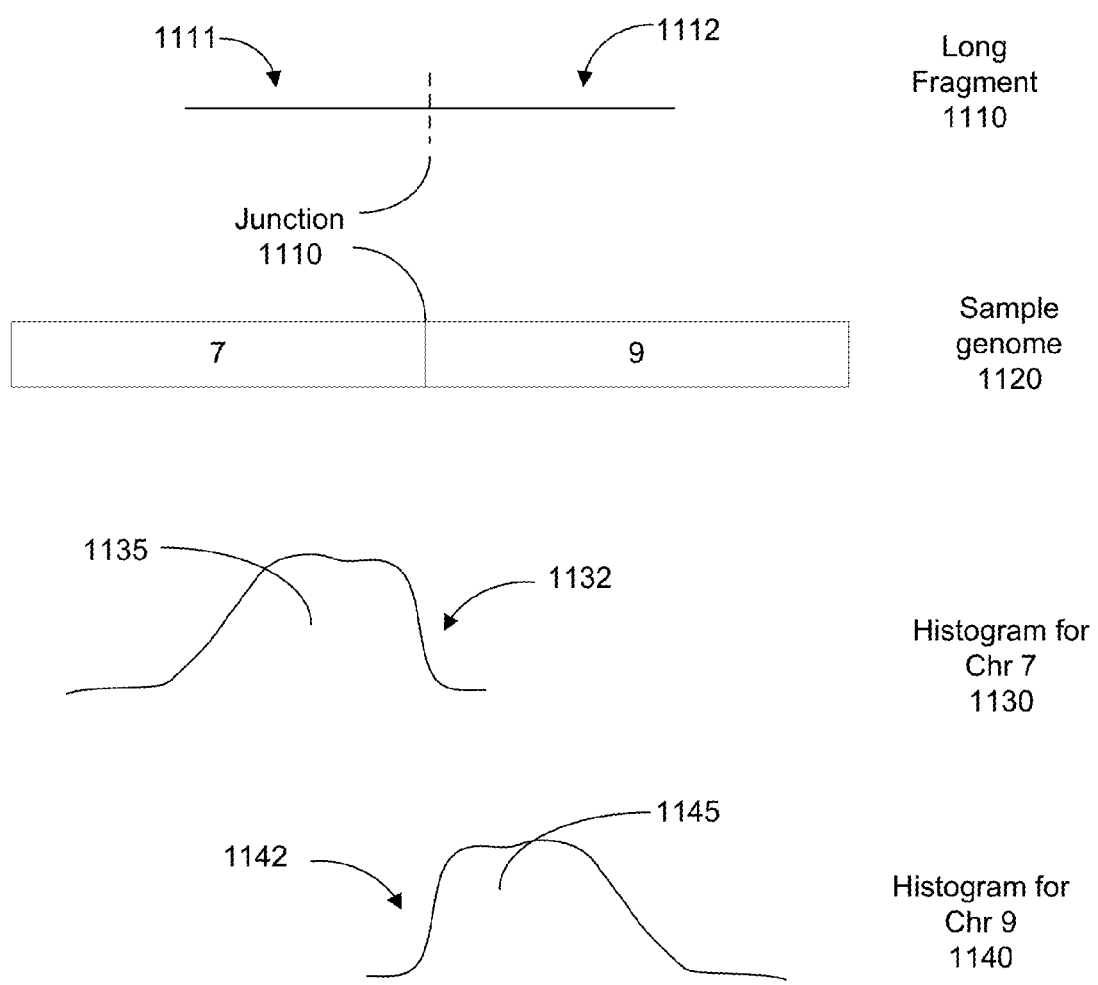
FIG. 11 shows an example structural variation where a portion of chromosome 9 is inserted into chromosome 7.

FIG. 11 shows an example structural variation where a portion of chromosome 9 (donor) is inserted into chromosome 7 (recipient). FIG. 11 shows a long fragment 1110 (e.g. from a well), the sample genome 1120 with a structural variation, a histogram 1130 for Chr 7, and a histogram 1140 for Chr 9. Junction 1125 indicates the point where the sample genome breaks from Chr 7 to Chr 9. As shown, the horizontal axis is genomic position. The inserted sequence could be from any chromosome (including Chr 7) or could be a novel sequence.

The long fragment 1110 spans the junction 1125 with a first part 1111 of the long fragment having a sequence corresponding to Chr 7 and a second part 1112 having a sequence that corresponds to Chr 9. As shown, the first part 1111 maps to Chr 7 (i.e. is situated at the same genomic position) and the second part 1112 maps to Chr 9. To restrict the analysis to coverage obtained from a same long fragment, LFR can be used to assume that all reads from a same well are from a same fragment. In one aspect, this assumption can be made since the fragments cover the chromosomes sparsely (for each well). Accordingly, once long fragment 1110 is broken into small fragments (e.g., in a well that contains about 10% of the genome) that are tracked, e.g., with a barcode, the system can produce histograms from the reads of the small fragments.

Histogram 1130 is created from the reads corresponding long fragment 1110 that map to Chr 7. The mapping is to the reference genome, which does not have the structural variation. Thus, only the reads from small fragments in the first part 1111 contribute to histogram 1130. As you can see, pulse 1135 in histogram 1130 roughly corresponds to the first part 1111. As the second part 1112 of long fragment 1110 does not map to Chr 7, histogram 1130 shows a sharp edge 1132 (e.g., which drops to zero) at junction 1110 where the first part 1111 ends. The opposite edge corresponds to the natural edge of long fragment 1110, and thus may be smeared (e.g., due to MDA fragmentation, as described above).

Histogram 1140 is created from the reads corresponding long fragment 1110 that map to Chr 9. The mapping is to the reference genome, which does not have the structural variation. Thus, only the reads from small fragments in the second part 1112 contribute to histogram 1140. As you can see, pulse 1145 in histogram 1140 roughly corresponds to the second part 1112. As the first part 1111 of long fragment 1110 does not map to Chr 9, histogram 1140 shows a sharp edge 1142 at junction 1110 where the second part 1112 starts. The opposite edge corresponds to the natural edge of long fragment 1110, and thus may be smeared.

Each of long fragments that cover the junction 1110 will also result in histograms similar to histograms 1130 and 1140. Regardless of the exact size and position of the long fragments, each of the histograms should show a relatively sharp edge at the junction 1110. When edges of the pulses in the histograms align (i.e. have a common increase or decrease) this is a sign of a break. For example, many sharp edges like 1132 can signify a break in the sample genome 1120 away from Chr 7. Also, simply the fact that a sharp exists can be used to identify a break (e.g., slope of the histogram being above a threshold). Once that break away from Chr 7 is correlated to the break in Chr 9, the junction can be identified. Knowing both parts of the junction can allow for assembly of the haploid genome. Note that typically both haplotypes would not have the same junctions.

Figure 12:
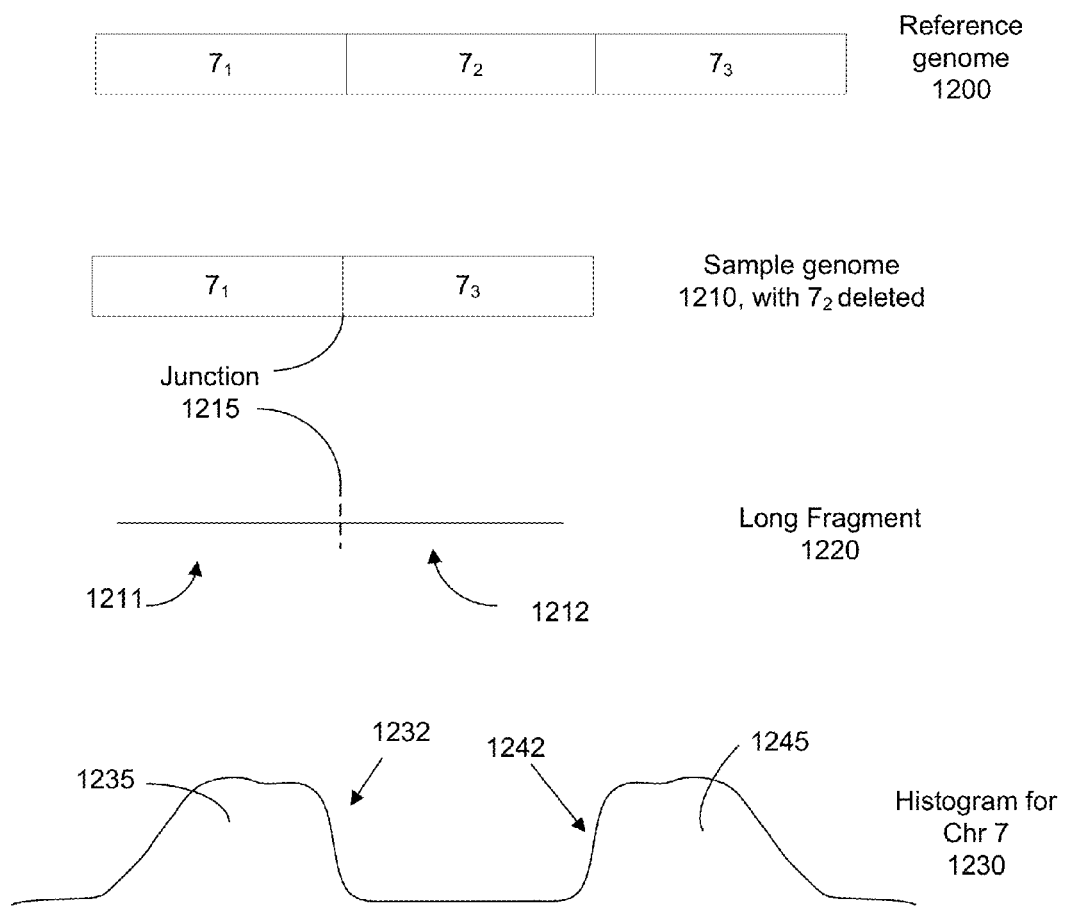
FIG. 12 shows an example structural variation where a portion of chromosome 7 is deleted.

FIG. 12 shows an example structural variation where a portion of chromosome 7 is deleted. As with FIG. 11, the horizontal axis is genomic position. Reference genome 1200 shows three segments of Chr 7, labeled as $7_1$, $7_2$, and $7_3$. The sample genome 1210 has segment $7_2$ deleted. Since the sample genome 1210 has a deleted segment, its scale of genomic position differs from the reference genome. Thus, segment $7_3$ is shown shifted to the left.

Long fragment 1220 of the sample spans the junction 1215. A first part 1211 of long fragment 1220 maps to segment $7_1$, while a second part 1212 of long fragment 1220 maps to segment $7_3$. A histogram of the reads corresponding to long fragment 1220 can similarly be analyzed to detect junction 1215. The histogram can be restricted to long fragment 1220 using techniques described above.

Histogram 1230 is created from the reads corresponding long fragment 1210 that map to Chr 7. The mapping is to the reference genome 1200, which does not have the structural variation. The reads of small fragments from the first part 1211 contribute to pulse 1235 (which corresponds to segment $7_2$), and the reads of small fragment from the second part 1212 contribute to pulse 1245 (which corresponds to segment $7_2$). But, none of the reads map to segment $7_2$, and histogram 1230 is left with a gap between pulses 1225 and 1245. The decreasing (falling) edge 1232 and the increasing (rising) edge 1242 result from segment $7_2$ being deleted. Once the two edges are correlated, the variation can be identified as a deletion. Thus, the two correlated edges can be from a same chromosome.

If the deletion were small, the distance between the falling and rising edges could be small. If the deletion were too small and total coverage (e.g. total number of well) sufficiently small, such a deletion could incorrectly be attributed to a lack of coverage or assumed to exist by being the mate gap, if clone coverage is used. But, small deletions can be identified directly from the arm reads themselves, where one read that happens to cover the deletion would identify the deletion.

Figure 13:
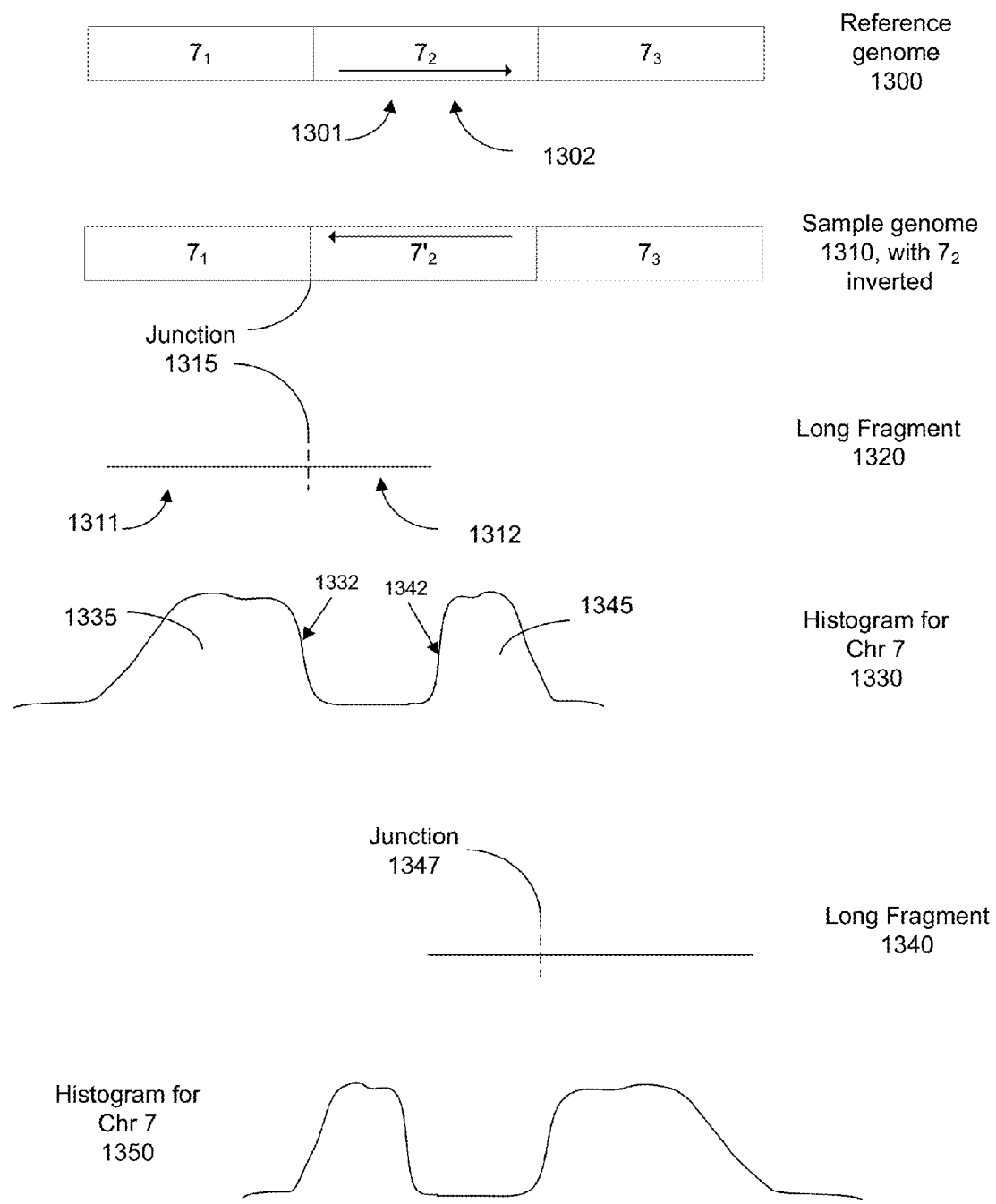
FIG. 13 shows an example structural variation where a portion of chromosome 7 is inverted.

FIG. 13 shows an example structural variation where a portion of chromosome 7 is inverted. As with FIG. 12, the horizontal axis is genomic position. Reference genome 1300 shows three segments of Chr 7, labeled as $7_1$, $7_2$, and $7_3$. The sample genome 1310 has segment $7_2$ inverted, as signified by the arrow. Since the sample genome 1310 has an inverted segment, its scale of genomic position differs from the reference genome.

Long fragment 1320 of the sample spans the junction 1315. A first part 1311 of long fragment 1320 maps to segment $7_1$, while a second part 1312 of long fragment 1320 maps to a second portion 1302 of segment $7_2$. A histogram of the reads corresponding to long fragment 1320 can be analyzed to detect junction 1315. The histogram can be restricted to long fragment 1320 using techniques described above.

Histogram 1330 is created from the reads corresponding long fragment 1310 that map to Chr 7. The mapping is to the reference genome 1300, which does not have the structural variation. The reads of small fragments from the first part 1311 contribute to pulse 1335 (which corresponds to segment $7_2$), and the reads of small fragment from the second part 1312 contribute to pulse 1345 (which corresponds to portion 1302). But, none of the reads map to portion 1301, and histogram 1330 is left with a gap between pulses 1325 and 1345. The decreasing (falling) edge 1332 and the increasing (rising) edge 1342 result from segment $7_2$ being inverted, and long fragment 1320 not extending all the way through segment $7_2$.

It may be difficult to differentiate between a deletion of portion 1301 and the inversion shown. However, a long fragment 1340 that spans junction 1347 between segment $7_3$ and inverted segment $7'_2$ can be used to differentiate. If portion 1301 was deleted, then junction 1347 would not exist. Histogram 1350 can be used in a similar manner to identify junction 1347.

If a long fragment covers both junctions 1315 and 1347 (or two junctions of an insertion), then the corresponding histogram would likely not drop to zero or near zero. However, the coverage would drop as the number of reads would be reduced since the mate pairs would not properly map across the junction, and would be labeled as discordant mate pairs. This dip could be used to identify the junctions, particularly if used in conjunction with histograms corresponding to fragments that only span one of the junctions.

B. Method

Figure 14:
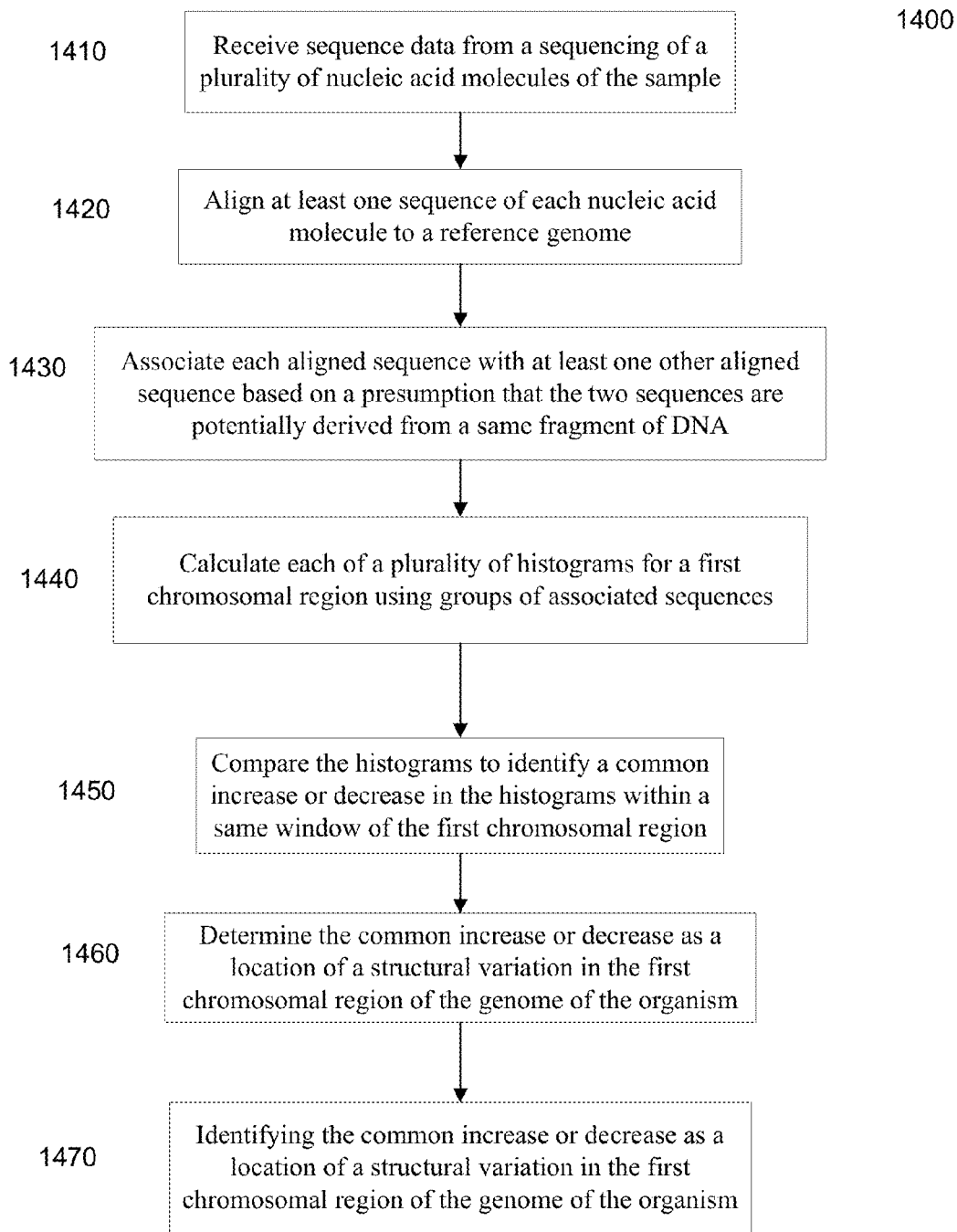
FIG. 14 is a flowchart illustrating a method of detecting a structural variation in a genome of a sample from an organism according to embodiments of the present invention.

FIG. 14 is a flowchart illustrating a method of detecting a structural variation in a genome of a sample from an organism according to embodiments of the present invention. Aspects of the discussion above can be used to determine structural variations. Such embodiments can be implemented as part of step 140 of method 100, or as a stand alone method. Some elements of other methods are repeated for clarity.

In step 1410, sequence data is received from a sequencing of a plurality of nucleic acid molecules of the sample. The sequence data includes sequences of at least one portion of each nucleic acid molecule. For example, the sequencing can be paired-end sequencing that results in two arm reads, which are called mated pairs. The nucleic acid molecules can be the small fragments described above.

In step 1420, at least one sequence of each of the plurality of nucleic acid molecules is aligned to a reference genome. The aligning (mapping) can be of the mater pair. Such aligning can account for typical lengths of small fragments to determine suitable matches for the mapping. As a result of such aligning, aligned reads are obtained with a mater gap between them, where the mate gap can be assumed to be the same as in the reference genome, although other sequence data can be used to change that assumption.

In step 1430, each aligned sequence is associated with at least one other aligned sequence based on a presumption that the two sequences are potentially derived from a same fragment of DNA (e.g., a long fragment). This association can be an association to a particular well, which may be identified via a barcode that had been attached to the nucleic acid molecules. Thus, the nucleic acid molecules with the same barcode (well ID) would be associated with each other. Two sequences can also be associated with each other by being the two arm reads of a mated pair.

In step 1440, a computer system calculates each of a plurality of histograms for a first chromosomal region. A respective group of sequences are identified as potentially being derived from a same fragment of DNA. For example, the barcodes can be used to identify the groups. All of the fragments would typically not come from the same fragment, but at this stage of the analysis, the sequences potentially could, depending on the length of the fragment. The sequences that map to the first chromosomal region can be counted for the histogram. The fragment includes at least a portion of the first chromosomal region to be analyzed in the histogram. A histogram can be limited to only the first chromosomal region, or be cover more of the genome than just the first chromosomal region.

Once the sequences are grouped, the histogram for each group can be created. In one embodiment, for each genomic position of a plurality of genomic positions within the first chromosomal region, a number of instances that an aligned sequence of the first group includes the genomic position is aggregated. For example, the information may be taken from a tally matrix, or aggregated by counting the sequences, or the histogram could simply be the tally matrix, or part of the tally matrix (e.g., the L counts).

In step 1450, the histograms are compared to identify a common increase or decrease in the histograms within a same window of the first chromosomal region. A series of co-occurring transitions (rising or falling) is referred to as breaks. A combination of breaks (falling to rising or the other way around) which have sufficient support (e.g. as defined by ratio of intersection of wells to union of wells) is referred to as a junction. A junction an be identified by correlating breaks, as is described below.

Many histograms can be compared to identify an area of a common rise or drop (which can correspond to a starting and ending edges of a pulse). If a variation does exist, many edges will exist at a same location (e.g., a range of relatively narrow width), whereas areas without a variation will have few edges. Embodiments can require the number of histograms with a common increase or decrease to be above a specified number, which can be an absolute number or a relative number (such as a percentage).

The size of a window can be about the size of a bin (e.g., about 1 kb), however other window sizes may be used, e.g., for greater resolution. In such a case, the criteria could simply be that the pulses start or end at the same bin. The window can be increased to prevent false negatives, i.e., missing windows of alignment because the window was too small. However, too large of windows can indicate false positives. However, false positives can be identified through a correlation step, which identifies a junction. Note that the common increase or decrease is a break as only one common edge may be identified, as opposed to the two correlated edges of a junction, which may be used to effectively remove false positives.

In step 1470, the common increase or decrease is identified as a location of a structural variation in the first chromosomal region of the genome of the organism. As mentioned above, the structural variation can be a break. Later correlation steps may provide an identification of a junction. The identification could include false positives. Later steps could correct such errant identifications.

Figure 15:
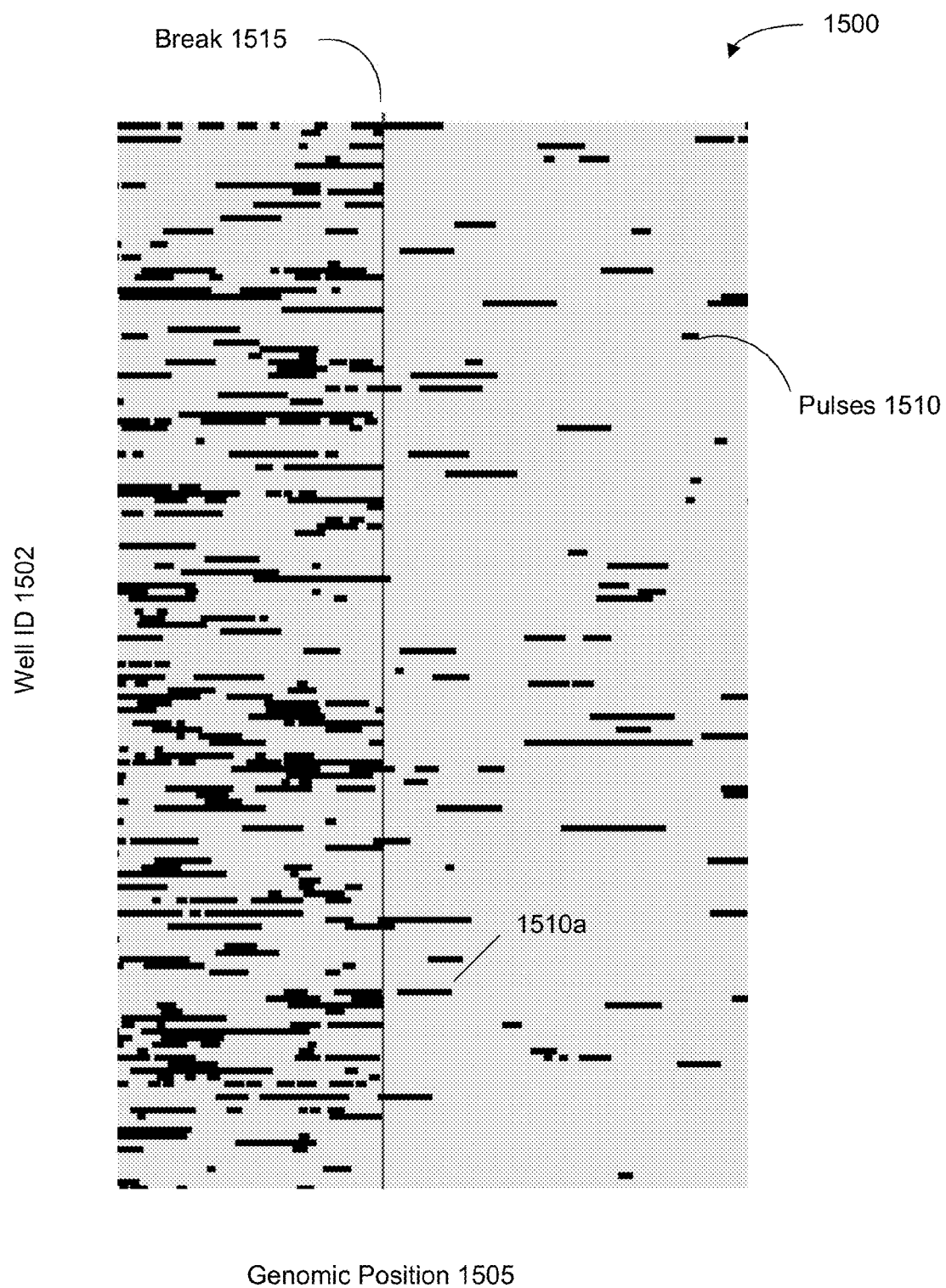
FIG. 15 is a plot 1500 showing the comparison of pulses to identify a common increase or decrease according to embodiments of the present invention.

FIG. 15 is a plot 1500 showing the comparison of pulses to identify a common increase or decrease according to embodiments of the present invention. The horizontal axis 1505 is genomic position for a particular chromosomal region of 650 kb. The vertical axis 1502 is well ID. Each row reflects the histogram for a respective well ID. Plot 1500 contains pulses 1510 interspersed between spans of little coverage. Thus, each horizontal row shows the pulses identified by embodiments described herein.

In FIG. 15, the genomic data was taken from a tumor. The pulses were generated by binning reads from individual barcodes for 1 kb bins. Both an amplification (as seen by an increased number of fragments) and a breakpoint (defined by many fragments ending at a specific place in the genome) were identified in the tumor. Pulse 1510a corresponds to a 50 kb fragment. In this example, on average, each aliquot (well) contained between 10-20% of a haploid genome in fragments with a median >50 kb.

At a single molecule level, viewed across the breakpoint 1515, chromosomal rearrangements would be expected to create sharp patterns of loss of coverage when mapped to a reference genome. The vast majority of fragments in tumor and normal samples showed no significant bias in location of ends points between wells. However, several hundred instances of fragments abruptly ending in unexpected regions of the genome were identified in each tumor. Importantly, 10-20 examples were found where a significant co-occurrence between fragment ends between different chromosomes were found.

Plot 1500 shows data for one such co-occurrence. As you can see there are pulses that start at different locations but all end close to the same location (break 1515), which suggests a variation. Similarly, a group of pulses starting at one location and ending at different locations would also signify a variation. In fact, a variation often has a falling edge (left of the junction) and an associated rising edge (right of the junction), which defines a junction.

C. Determining Cluster of Common Edges

Since step 1460 determines a common increase or decrease, the system can identify a co-occurrence of just one edge of a pulse with another edge of a pulse, where both edges are either the starting edge or both are the ending edge. When the edges are due to a structural variation, the edges should be sharp. The edges that are not part of the pair (i.e. way from the structural variation) my taper off slowly, but the exact location of the farther edge does not matter for identifying a location of a structural variation. Thus, both edges of a pulse do not need to be identified. Since variations are typically associated with sharp edges, certain edges can be filtered out (e.g., by looking at the slope of the edge) so that only likely edges are analyzed to determine a co-occurrence of the edges. This can reduce the number of false positives since only sharp edges are being investigated.

The search for co-transitions in pulses can be referred to as clustering. Ordinarily, the pulses are independent. However, when a structural variation occurs, since the two parts do not belong to the same area, there would be an abrupt lack of continuity for the donor and recipient segments. Various methods may be used for such clustering. One implementation is to use a moving window on the genome. For each window, the number of the found pulse endings are counted. If, for one window, the counts are above a certain background, then that window could be a candidate for a structural variation break.

In one embodiment, the window size is a function of the small fragment size, e.g., when the clone coverage is used. In some examples, 1 Kb is about two times the small fragment size. In another embodiment, multiple window sizes may be used. For example, one window can be used to find a possible cluster, and then other windows with a more limited scope and higher resolution may be used to find finer features, e.g., to refine the cluster with criteria for the number of breaks within a cluster.

Figure 16:
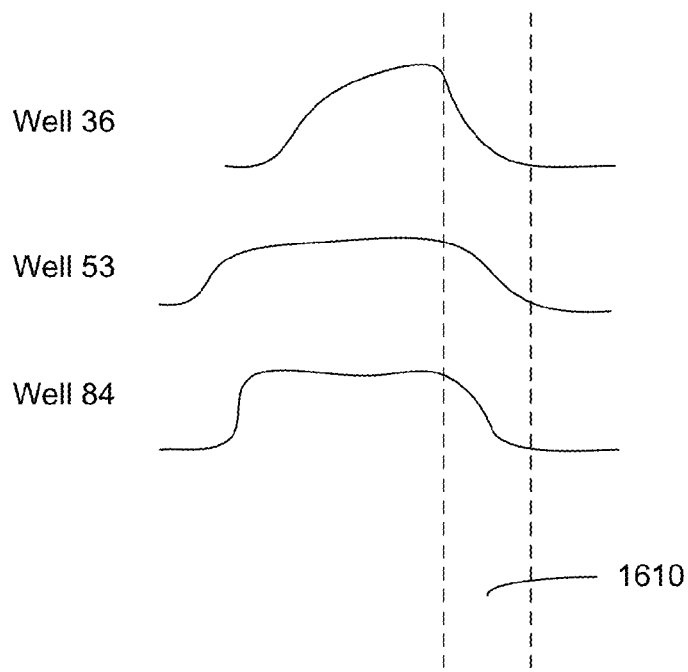
FIG. 16 shows a co-occurrence of pulse edges according to embodiments of the present invention.

FIG. 16 shows a co-occurrence of pulse edges according to embodiments of the present invention. Histograms for wells 36, 53, and 84 are shown. As shown, each of the pulses have a falling edge that falls within window 1610. Window 1610 could be a moving window of fixed size that sweeps through the histograms for each well to determine when a sufficient number of pulses have an edge. This may be done when pulse edges are already determined, or the pulse edges could be determined based on the histograms within the specific window.

In other embodiments, one edge can be identified as being sharp, and then one or more windows of varying sizes can be tested to identify whether a sufficient number of common edges are found in the window. Thus, if an edge is very well-defined (e.g. slope is above a certain value), it can be used as an indicator of a structural variation. The indicator can then be used to identify pulses whose edges should be checked for corresponding edges of other pulses to determine if a break exists.

D. Refining Location of Break

Once a cluster of synchronized edges (i.e. pulse edges of the same type within a window), the exact location can be taken as the window or can be refined to a smaller region than the window. As mentioned above, the refinement can involve using smaller window sizes around some median point (e.g. an initial estimate of the edge based on one or more of the pulse edges), where a raw histogram (i.e. no averaging or a smaller bin) can be used for the smaller windows. However, other techniques can also be sued.

In one embodiment, the histograms for the various wells of the cluster can be combined in the vicinity of the initial estimate of the breakpoint. For example, the clone coverage from such wells can be added up into one histogram, which can provide greater resolution for identifying the breakpoint. Combined histogram 1630 in FIG. 16 shows an example of such an aggregation. A combined histogram is likely to provide a better estimate as the total drop will be larger than for just one well. Also, with more wells, there is a greater statistical probability that reads very close to the breakpoint will be obtained, which can give greater resolution.

The combined histogram can also be checked for criteria to confirm the break. For example, if the slope of the combined histogram is not large enough then the location can be dismissed and not considered to result from a variation.

Additional data can also be used for confirmation of a break and refinement of the location. For example, reads from discordant mate pairs that map to the genomic region within a window around the estimate breakpoint can also be included in the combined histogram. If a small fragment spans the break, the a corresponding mate pair usually is not mapped and is not used. However, the individual arm reads could still be mapped, and are likely close to the true breakpoint.

Additionally, some arm reads are not assigned to a well due to problems in reading barcode. Such mated reads may map to the reference genome, but just cannot be assigned to a particular well for use in identifying a pulse. Such arm reads are discussed above regarding barcode error. Such arm reads can be labeled as well 0, which does not physically exist. Once a window has been identified to determine the breakpoint, arm reads that have no well assignment, but do map to the region can also be added to the combined histogram.

As other examples of refinement, one can take the average edge location of each one of the pulses in the cluster. Or, one could take the farthest edge as this one might be the closest one to the actual junction simply because it happened to include an arm read at the junction, as opposed to one 20 nt before the junction.

Where well 0 is used, the drop may not be to zero as these arm reads could come from pulses that anywhere in the genome. Where fragments are tracked with a well ID and the genomic equivalents per well is low (e.g., ~0.1), the drop in the combined histogram would most likely be to zero since only one copy of any particular genomic region would likely be in the well.

E. Correlating Decreases and Increases

Once a potential break has been identified (i.e. any identified break at this point), the system can attempt to correlate the identified break with another identified break as part of determining a junction. This determination of a junction can provide the sequence on either side of the junction. Note that a well could have many clusters of edges, with each cluster corresponding to an identified break.

Figure 17:
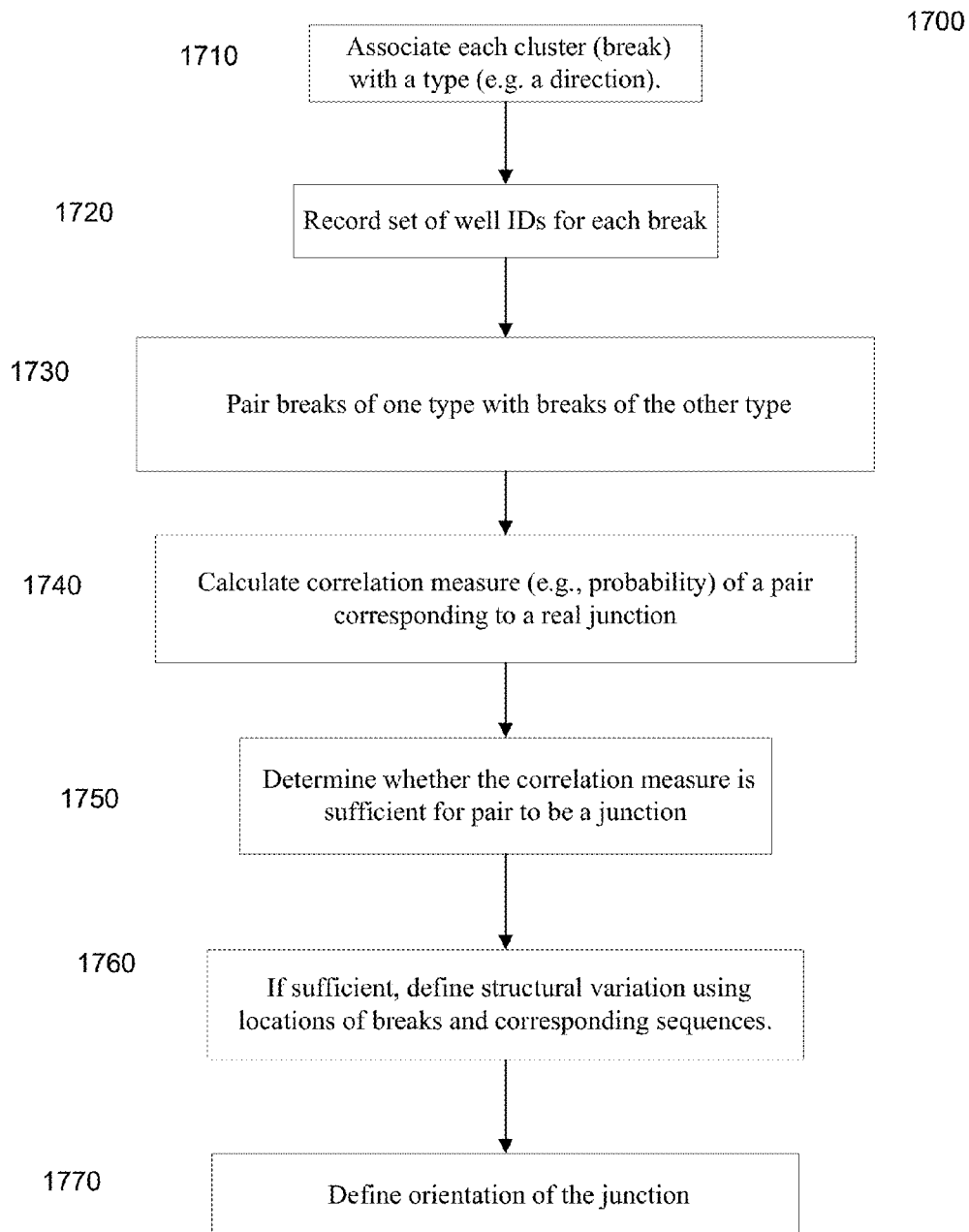
FIG. 17 is a flowchart illustrating a method 1700 for correlating breaks to determine a junction according to embodiments of the present invention.

FIG. 17 is a flowchart illustrating a method 1700 for correlating breaks to determine a junction according to embodiments of the present invention. A plurality of breaks can be identified, with a cluster of edges corresponding to each break. Two breaks can be correlated to determine the sequence on either side of the junction in the sample genome.

In step 1710, each identified break (cluster) is associated with a type. There are two types, which can correspond to rising and falling edges. In one embodiment, the types can be characterized as a direction. This direction reflects the shape of the pulse at that junction, i.e., either a falling edge or a rising edge. Different types are correlated with each other.

In step 1720, for each break, a set of well IDs is recorded. Each pulse has an associated well ID, and a break is composed of a cluster of pulses. Thus, a break has a set of one or more well IDs. The breaks, even of the same type, could have the same well ID in their respective set of well IDs. Thus, two breaks can share a common subset (intersection) of well IDs.

In step 1730, the breaks of one type are paired with breaks of the other type. The pairings can be searched in an exhaustive manner to find the junctions. A junction is composed of a break of each type (e.g., one falling edge and a rising edge). Assuming there are 900 falling edge breaks and 1000 rising edge breaks, then there would be 900*1000=900,000 combinations to check. The breaks of a pair can be from the same chromosome, e.g., the recipient and the donor could be from the same chromosome.

Figure 18:
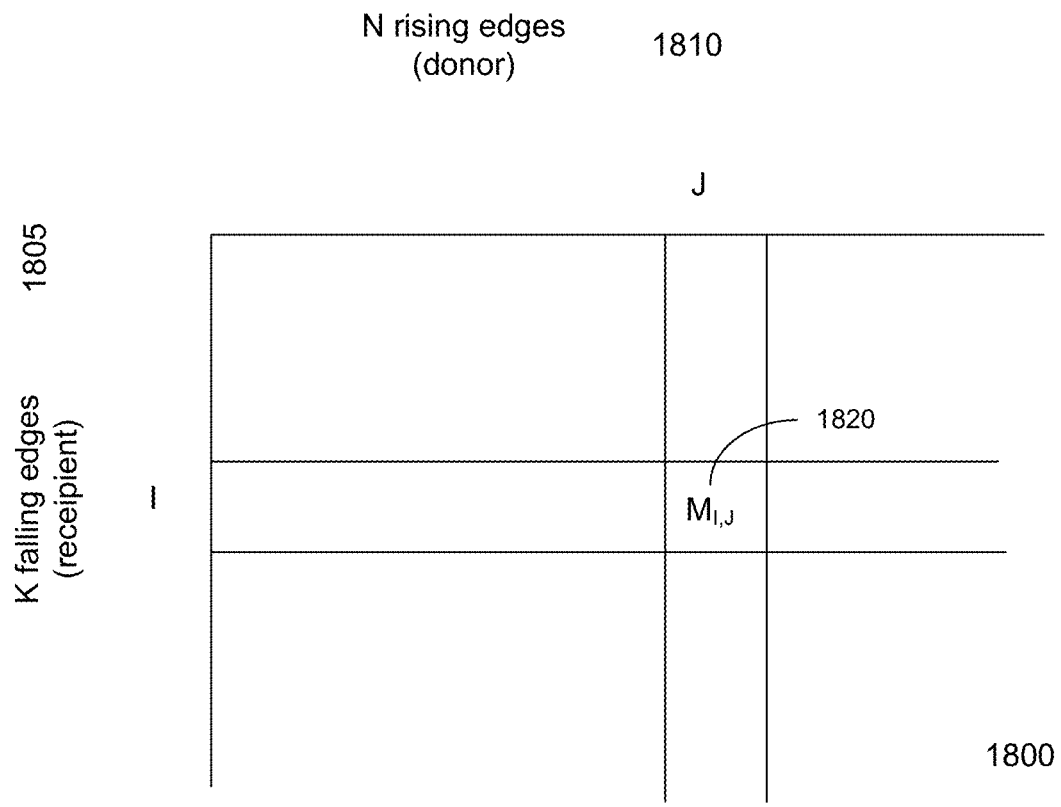
FIG. 18 is a matrix 1800 showing pairings of the two types of breaks.

In one embodiment, a matrix can be defined for the pairings. FIG. 18 is a matrix 1800 showing pairings of the two types of breaks. The rows 1805 are for K falling edges, e.g., corresponding to a recipient genomic region. The columns 1810 are for N rising edges for N rising edges, e.g., corresponding to a donor genomic region. The matrix element are discussed below.

In step 1740, a correlation measure of a pair corresponding to a real junction is calculated. The correlation measure can be determined as a figure-of-merit that reflects the probability of a real junction. The probability value between the Ith rising break and the Jth falling break can be stored as the matrix element $M_{I,J}$ labeled 1820. The probability value can be determined using the wells in which the breaks are detected. If a long fragment does cover a junction, then the two resulting breaks should be detected in the same well. Thus, a correlation can be determined if a decrease in one region is seen to occur on a same long fragment as an increase in another region, and a calculation can determine many fragments show both the increase and decrease (e.g., as determined by how many wells show both the increase and decrease).

One example measure could simply use the number of wells in common between the two breaks. Another example measure (figure-of-merit) is the ratio of the number of wells in common divided by the number of wells among the two breaks. Such a measure can be expressed as the intersection of the two sets of wells IDs for the two clusters divided by the union of the well IDs corresponding to the two clusters. The total number of wells where the two breaks are found can act as a normalization factor.

To implement this example, the system can create a list of the wells for each break. Then a matrix element would be the intersection $\cap_{wells}$ of the two lists divided by the union $\cup_{wells}$. The matrix element would be $\cap_{wells}/\cap_{wells}$. For example, if falling edge $K_{14}$ was found in wells {2, 9, 53, 380} and rising edge $N_{78}$ was found in wells {1, 9, 53, 380, 382}, then $\cap_{wells}$ would be three for {9, 53, 380} and $\cup_{wells}$ would be six for {1, 2, 9, 53, 380, 382}. In this case, the figure of merit would be 0.5.

Additionally, the number of wells in common can be a weighted average. This technique can be made more robust by using scores associated with pulse edges. Depending on how sharp of an increase or decrease is detected, a pulse/well combination can be associated with a particular score (e.g., in the range of 0 and 1), which can help eliminate false positives. As an example, assume that there are 4 wells in common, with the rising break having scores of {0.3,0.7, 0.5,0.9} and the falling break having scores of {0.4,0.6,0.6, 0.8}. The total could sum these values, which could be normalized (e.g. by dividing by 2). Further normalization by the total number of wells, which can also count for the scores, can also be done. If the score for a well is week, the well could also be removed from the set of wells for a break. Such pulses/wells with a low score could just be noise. An overall score could be determined for a break by the spread in the location of the edges of the break.

In step 1750, it is determined whether the correlation measure is sufficient for the pair to be a junction. For example, if the measure exceeds a threshold, then the pair can be identified as a junction. In one implementation, the number of common wells can be compared to predetermined number, e.g., 5 wells. In another embodiment, the figure-of-merit $\cap_{wells}/\cup_{wells}$ can be compared to a threshold (e.g. 0.1), which could be fixed or determined from the other matrix elements. For example, the correlation value can be required to be sufficiently larger (e.g. a fixed amount more or a percentage more) than other measures (particularly ones involving the same break). As another example, the threshold can be a function (e.g., nonlinear) of the minimum number of wells (for falling and rising). To prevent measures with low statistical value, the union can be required to higher than a certain minimum. Thus, even if one well for each corresponds, the matrix element might be set to zero since the union is only 1, and below a minimum threshold (e.g. of 3). If the correlation measure is sufficient, this can provide confirmation that a break does indeed exist; otherwise, the identified break could be rejected as not being actually in the sample genome.

Ideally one matrix element in a row is above the threshold, which can confirm the proper pairing. If there are more than one matrix element above the threshold, then it can be investigated more. This could result from a mismapping. In some cases, two matrix element could rightfully be above a threshold. For example, if a deletion is relatively small (e.g. 1 kb), then many large fragments can span both junctions associated with the deletion.

In step 1760, once a junction is established, the structural variation can be defined by the two breaks and the corresponding sequences of the pulses used to identify the breaks. For example, the segment corresponding to the falling edge is to the left of the junction, and conversely, the segment corresponding to the rising edge is to the right of the junction.

Some embodiments can detect a variation due to the incorporation of the DNA of another organism. For example, embodiments could detect the insertion of a viral DNA into a human DNA. The DNA of the other organism can be considered as an extra set of chromosomes added to the original organism's genome.

In step 1770, the system can define the orientation of the junction (e.g., as an inversion or not). This may be done in various ways. One possibility is to find mate pairs that span the edge. By trying the two orientations, and finding which one results in more mate pairs, one could establish the orientation. However, this may not be suitable due to the small number of candidate mate pairs for the junction region, and the erosion around the pulse edges, due to the scarcity of the mate pairs on a particular well, in LFR.

In another embodiment, the mapping is done not only to the reference genome, but also considering the inverted genome. The inversions can, then, be detected by finding high well correlation between a cluster on the regular genome, and another one on the inverted genome. Once again, a relationship can be established by having a falling edge for the donor and a rising edge for the acceptor segments.

Once the orientation is determined, the sequence of the sample genome on either side of the junction can be determined. For example, in FIG. 10, it can be determined that a specific portion of Chr 9 is inserted in Chr 7. Or, the inversion of segment $7_2$ can be determined. Such assembly can occur at any point, and can result in a more accurate haploid genome.

In some embodiments, the insertion can be of a novel sequence, where the arm reads of the novel sequence would not map to the reference genome. These non-mapped reads can be compared against a database of possible novel insertions in order to identify a junction. But if no match is found in the database or such a step is not performed, a correlation might not be seen since no mapping of arm reads is performed for the novel sequence. If the novel insertion was small enough than a correlation of the two breaks in the recipient chromosome might be correlated. But, if none of these scenarios apply, the break could be investigated more if certain criteria apply. For example, if the edge was sharp enough, then the break might not be thrown out. In such a case, the non-mapped arm reads from the wells showing the break could be assembled to identify the inserted sequence.

Besides novel sequence, some areas of genome are not known, e.g., neat the centromere, the ends, or certain areas (such as poly N regions) that are harder to sequence. These may show false positives. These areas can be identified and ignored when they show up as potential breaks.

VIII. Phasing

Once long fragments are recreated from the identified pulses and the related arm reads, these long fragments can be phased. The phasing can identify each long fragment as belonging to parent 1 or parent 2, or at least group certain long fragments into groups of consistent sequences. More than two groups can exist at first, but as further analysis occurs the groups can be merged into just two groups. Note that for single individual haplotyping, each chromosome would have two groups, i.e., one from each parent. But, one does not know which group (haplotype) of Chr 1 is from the same parent as a group (haplotype) of Chr 4. The process of grouping (clustering) the long fragment can be performed in various ways, and may be done in step 150 of method 100.

In one embodiment, the system can look at the heterozygous loci (hets) of the sample genome and determine which long fragments are consistent with each other, and thus should be on the same haplotype. Effectively, the system can create two clusters that are consistent with each other based on analyzing one het at a time, two hets at a time, or more.

Figure 19:
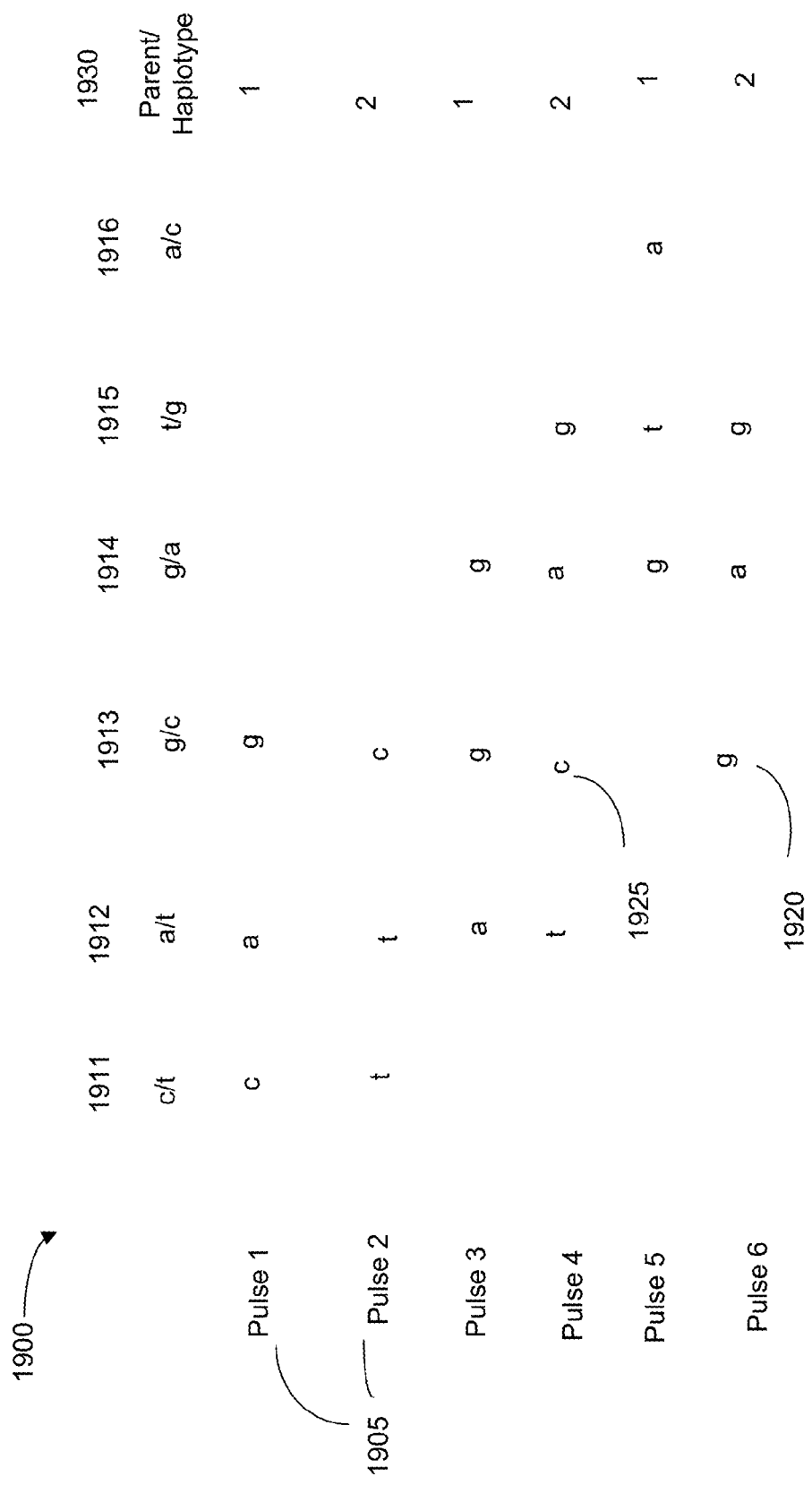
FIG. 19 shows a diagram 1900 illustrating a phasing of long fragments.

FIG. 19 shows a diagram 1900 illustrating a phasing of long fragments. Several pulses 1905 are shown with a respective allele at one of hets 1911-1916. The hets are shown as having two possible alleles. As shown, pulse 1 and pulse 3 are consistent at hets 1912 and 1913. Thus, both can be put into the cluster corresponding to parent 1, as shown in column 1930. Pulse 5 is then consistent with pulse 3 at het 1914; therefore, pulses 1, 3, and 5 can be put into the group of parent 1. Thus, one can start at one het, and determine pulses that belong to a haplotype. From there, one can add other pulses to the each of the two clusters by looking at the other hets on the initial pulses of a cluster.

However, some data can be inconsistent. For example, pulse 6 has G at het 1913, which would seem to make it consistent with parent 1, but it has alleles at hets 1914 and 1915 that are not consistent with parent 1, but are consistent with parent 2. There are several techniques for performing clustering even when such errors exist. For example, different criteria can be used for changing allele values or minimum fragment removal (MFR), minimum error correction (MEC), and minimum SNP removal (MSR) [Bafna, V. et al. (2003) Haplotyping as perfect phylogeny: a direct approach. J. Comput. Biol., 10, 323-340; Cilibrasi, R. et al. (2005) On the complexity of several haplotyping problems. In Casadio, R. and Myers, G. (eds), WABI, Vol. 3692 of Lecture Notes in Computer Science, Springer, Berlin, pp. 128-139; Lancia, G. et al. (2001) SNPs problems, complexity and algorithms. In Proceedings of the Ninth Annual European Symposium on Algorithms (ESA) Springer, Berlin, pp. 182-193]. Other techniques define a distance between fragments and perform clustering based on the distance [Suk, E. et al. (2011) A comprehensively molecular haplotype-resolved genome of a European individual. Genome Res., 21, 1672-1685].

The above techniques assume that only two alleles are ever measured at any one genomic position. However, there can be more than two alleles measured for various pulses due to errors. FIG. 10 showed such an example. If there are multiple bases at a het, one can employ clustering techniques as described for FIG. 10.

Accordingly, long fragments on the order of 100 Kb for different wells can be combined. SNP data (which can be identified by doing assembly without using the well IDs) can be used at this point, e.g., to identify the two likely alleles. For each two long fragments that are overlapping, one could interrogate the heterozygous loci, and if there are a sufficient number of them in agreement, the two fragments (from different wells) can be joined. In an alternate approach, a multiple alignment of some overlapping fragments is done. Then, these aligned fragments can be clustered using the similarity in the heterozygous regions. Two clusters are expected as the fragments belong to one of the two parental chromosomes. The fragments for each of the two clusters can then be combined in an assembly procedure.

IX. Assembly

Once the recreated long fragments are grouped into clusters (e.g., two groups for each chromosome or two groups for each arm of the chromosome), the groups can be assembled to determine the sequence of the haplotypes. The assembly can use information about structural variations and can look at resolving errors in base calls. Embodiments of assembly can be may be done in step 160 of method 100.

Normally, one would have a support table from all of the data for the diploid genome, e.g., as shown in the support table. Typically, assembly would only result in the genotypes of each location, for which data is obtained. That is, for each location, all we get is the one base call for a homozygous location and two base calls for a heterozygous location. However, the data of the table can be ambiguous or incorrect, particularly if a limited amount of data is available. For example, there may be a small amount of base calls so that a location is ultimately determined as a no call. Or, for a potentially heterozygous location, one of the alleles may be determined as a no call. For example, since there is noise. Thus variation can be from noise, and not from actual variation at a location (e.g., an actual SNP). There would need a lot of data to suppress the noise (e.g., more sequencing coverage, which costs more). However, here, we can group the data by haplotype. In this manner, some of the no calls or other errors can be corrected.

FIG. 20 shows a diagram illustrating an assembly process that can use the haplotype clusters of the pulses to resolve ambiguities in the basecalls of the haploid genome. A reference genome 2000 is shown for a series of base positions. Typically an assembled genome is the diploid genome, which involves just the base calls at the positions, without any correlation of alleles to a specific haplotype. An assembled diploid genome 2010 is shown just below reference genome 2000. The genomic positions are aligned.

Support table 2020 provides the number of basecalls of the arm reads at each of the listed positions. The first four positions only have calls for one base, and thus the values at these four positions is clear. Position 2015 in assembled diploid genome 2010 is identified as likely being heterozygous. For position 2015, there are 7 calls for A, 1 for G, and 6 for T. Although there is one call for G, the system can still identify this position as being A/T since 6 and 7 are much higher than 1. Different embodiments can implement such decisions differently.

Position 2017 is identified as N/T to show that T is likely, but the other base is not certain. This ambiguity can result from both C and G showing one base call. If these arm reads came from the same haplotype as the reads providing 3 calls for A, then there would only be a weak majority of A calls. But, if the basecalls were separated out by haplotypes, the identification of the base call could be easier.

Support table 2030 shows the counts for haplotype I and support table 2040 shows the counts for haplotype II. These support tables shows how the data for what was a no call of het 2017 can more clearly be identified as an A instead of an N. In a haploid genome one does need to worry about the possibility of more than one base (as there is for the diploid genome), and the system just needs to determine if there is sufficient evidence to make a base call. As shown, once the counts are broken down into the two haploid genomes, the system can more easily identify Hap I as having A, since there are three A occurrences and just one C. The C call can then be removed as being an error. Whereas, if that haploid showed, 3 A, 1 C, and 1 G, then this data might be considered too noisy and the actual base call would be uncertain. Such assembly can be broken down into more than two haploids, e.g., for trisomic genomes, where there are three distinct haploids (e.g. for a particular genomic section).

X. Computer System

Figure 21:
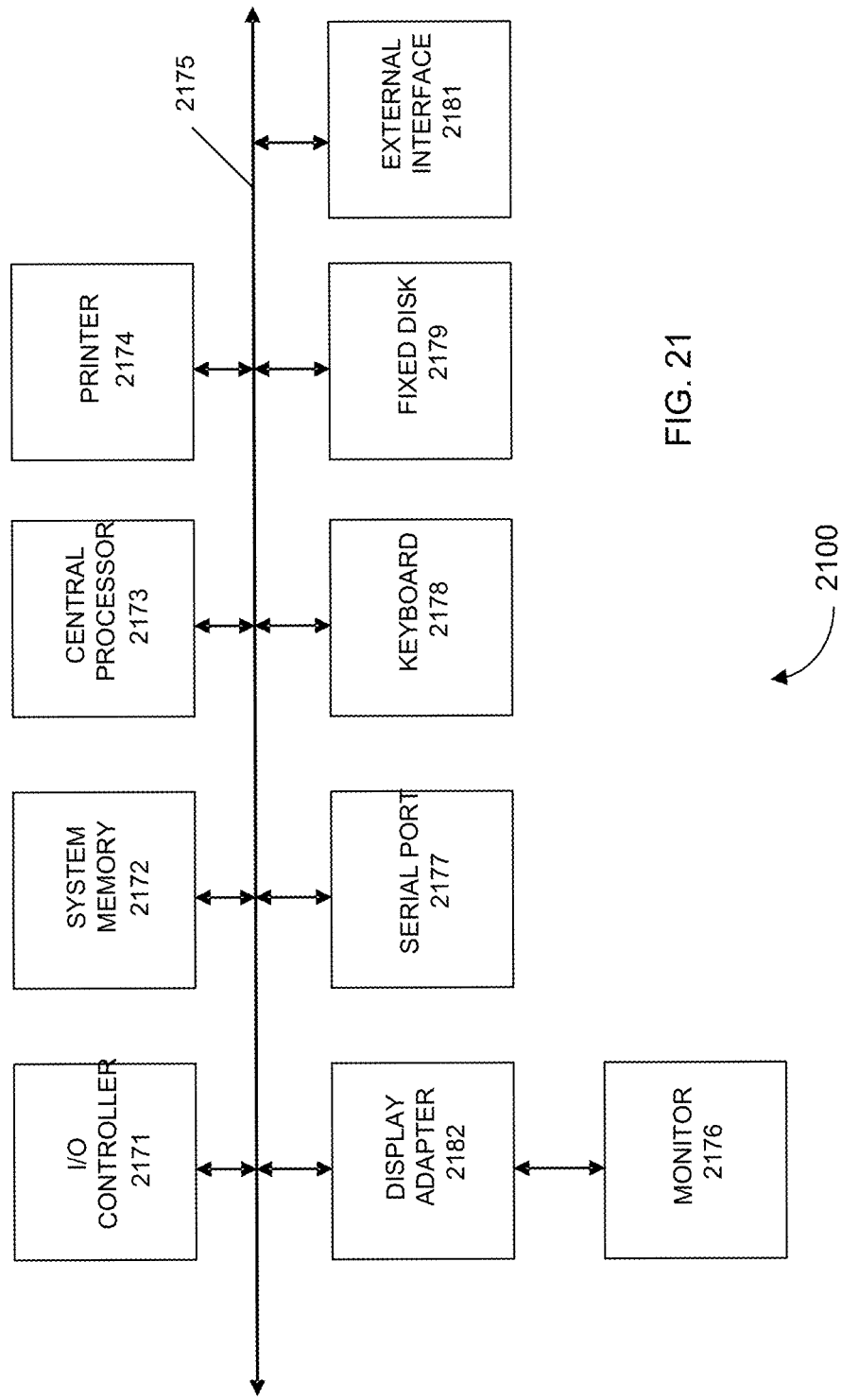
FIG. 21 shows a block diagram of an example computer system 2100 usable with system and methods according to embodiments of the present invention.

Any of the computer systems mentioned herein may utilize any suitable number of subsystems. Examples of such subsystems are shown in FIG. 21 in computer apparatus 2100. In some embodiments, a computer system includes a single computer apparatus, where the subsystems can be the components of the computer apparatus. In other embodiments, a computer system can include multiple computer apparatuses, each being a subsystem, with internal components.

The subsystems shown in FIG. 21 are interconnected via a system bus 2175. Additional subsystems such as a printer 2174, keyboard 2178, fixed disk 2179, monitor 2176, which is coupled to display adapter 2182, and others are shown. Peripherals and input/output (I/O) devices, which couple to I/O controller 2171, can be connected to the computer system by any number of means known in the art, such as serial port 2177. For example, serial port 2177 or external interface 2181 (e.g. Ethernet, Wi-Fi, etc.) can be used to connect computer system 2100 to a wide area network such as the Internet, a mouse input device, or a scanner. The interconnection via system bus 2175 allows the central processor 2173 to communicate with each subsystem and to control the execution of instructions from system memory 2172 or the fixed disk 2179, as well as the exchange of information between subsystems. The system memory 2172 and/or the fixed disk 2179 may embody a computer readable medium. Any of the values mentioned herein can be output from one component to another component and can be output to the user.

A computer system can include a plurality of the same components or subsystems, e.g., connected together by external interface 2181 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware (e.g. an application specific integrated circuit or field programmable gate array) and/or using computer software with a generally programmable processor in a modular or integrated manner. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C++ or Perl using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer program product (e.g. a hard drive, a CD, or an entire computer system), and may be present on or within different computer program products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of exemplary embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

A recitation of "a", "an" or "the" is intended to mean "one or more" unless specifically indicated to the contrary.

All patents, patent applications, publications, and descriptions mentioned above are herein incorporated by reference in their entirety for all purposes. None is admitted to be prior art.

What is claimed is:

1. A method of detecting a structural variation in a genome of a sample from an organism, the method comprising:
   providing a plurality of aliquots, each aliquot comprising nucleic acid molecules of the genome that have barcodes to track from which aliquot a nucleic acid molecule originates, wherein each of the plurality of aliquots includes less than a genomic equivalent of the genome of the organism;
   sequencing a plurality of nucleic acid molecules in the plurality of aliquots to obtain sequences of the plurality of nucleic acid molecules and the barcodes;
   receiving, at a computer system, sequence data from the sequencing the sequence data including sequences of at least one portion of each nucleic acid molecule of the plurality of nucleic acid molecules, wherein the sequence data includes the barcodes for tracking from which aliquot a sequence originates;
   for each of the plurality of nucleic acid molecules:
      aligning, with the computer system, at least one sequence of the nucleic acid molecule to a reference genome;
   for each of the plurality of aliquots, calculating, with the computer system, a histogram for a first chromosomal region by:
      identifying a respective group of sequences as being derived from a same fragment of DNA based on the barcodes of the respective group of sequences corresponding to a same aliquot, the same fragment including at least a portion of the first chromosomal region;
      for each genomic position of a plurality of genomic positions within the first chromosomal region:
         aggregating a number of instances that an aligned sequence of the respective group includes the genomic position;
      comparing the histograms to identify a common increase or decrease in the histograms within a same window of the first chromosomal region as a location of the structural variation in the first chromosomal region of the genome of the organism.

2. The method of claim 1, wherein the structural variation is an insertion of a novel sequence, insertion of a sequence from a different chromosomal region of a different chromosome or a same chromosome, deletion, or inversion of a portion of the first chromosomal region.

3. The method of claim 1, further comprising:
identifying common increases and decreases in histograms of other chromosomal regions, wherein the first chromosomal region is identified as having a first decrease in the corresponding histograms;
correlating the first decrease in the first chromosomal region with a second increase in a second chromosomal region;
determining the first decrease and the second increase to be part of a same structural variation;
determining that the first chromosomal region and the second chromosomal region are proximal to each other in the genome of the organism.

4. The method of claim 3, wherein correlating the first decrease in the first chromosomal region with the second increase in the second chromosomal region includes:
determining a first value from a first number of fragments of DNA that include both the first decrease and the second increase; and
comparing the first value to a threshold to determine that a correlation does exist when the first value is greater than the threshold.

5. The method of claim 4, wherein comparing the first number to the threshold includes:
calculating a function of the first value to obtain a first result; and
comparing the first result to the threshold, wherein the function is a ratio of the first value divided by a total number of fragments used to determine the structural variations in the first and second chromosomal regions.

6. The method of claim 5, wherein the first value is a number of fragments of DNA that include both the first decrease and the second increase.

7. The method of claim 5, further comprising:
assigning a respective score to the first decrease and the second increase, wherein the score reflects a likelihood that the increase or decrease exists, wherein the first value is a weighted sum that accounts for the respective scores.

8. The method of claim 5, further comprising:
assigning a respective score to each fragment of DNA that is identified as including both the first decrease and the second increase, wherein the first value is a weighted sum that accounts for the respective scores.

9. The method of claim 3, wherein correlating the first decrease in the first chromosomal region with a second increase in the second chromosomal region includes:
determining a number of pairs of arms reads from a same nucleic acid molecule that have:
a first arm read that aligns to the first chromosomal region; and
a second arm read that aligns to the second chromosomal region; and
comparing the first number to a threshold to determine that a correlation does exist when the first number is greater than the threshold.

10. The method of claim 3, further comprising:
comparing the first number of fragments to one or more additional numbers of fragments of DNA that include both the first decrease and at least one other increase of at least one other chromosomal region.

11. The method of claim 3, further comprising:
correlating a third increase in a third chromosomal region with a fourth decrease in a fourth chromosomal region;
determining the third decrease and the fourth increase to be part of a same structural variation, wherein the structural variation is an insertion of the third chromosomal region into the fourth chromosomal region; and
determining that the third chromosomal region and the fourth chromosomal region are proximal to each other in the genome of the organism.

12. The method of claim 1, further comprising:
identifying that two sequences of a group of sequences are derived from the same fragment of DNA based on the two sequences being of opposite arm reads of a nucleic acid molecule.

13. The method of claim 1, wherein identifying the common increase or decrease as the location of the structural variation in the first chromosomal region of the genome of the organism includes:
calculating a measure of the common increase or decrease;
comparing the measure to a threshold; and
determining that a structural variation exits when the measure is greater than the threshold.

14. The method of claim 13, wherein calculating the measure of the common increase or decrease includes:
aggregating the histograms exhibiting the common increase or decrease of the first chromosomal region to obtain a total histogram, wherein the calculating the measure uses values from the total histogram.

15. The method of claim 13, wherein calculating a measure of the common increase or decrease includes:
obtaining a maximum value from one or more of the histograms;
obtaining a minimum value from one or more of the histograms;
calculating a difference between the maximum value and the minimum value; and
comparing the difference to a difference threshold to determine if a structural variation exists.

16. The method of claim 1, further comprising:
determining the window of the first chromosomal region for identifying the common increase or decrease.

17. The method of claim 1, further comprising:
determining when an aligned sequence of the respective group includes a particular genomic position by:
receiving two arms reads of the aligned sequence, the two arm reads being aligned to the reference genome; and
determining that the aligned sequence includes any genomic positions between the two arm reads.

18. The method of claim 1, wherein comparing the histograms to identify the common increase or decrease in the histograms within the same window of the first chromosomal region includes:
determining a genomic location of a pulse in a histogram;
identifying a beginning of the pulse as an increase in the histogram; and
identifying an end of the pulse as a decrease in the histogram.

19. The method of claim 18, wherein determining the genomic location of the pulse in a histogram includes:
determining a set of continuous genomic positions with histogram values above a detection threshold; and
identifying the set as a first pulse, wherein the beginning of the first pulse is associated with a first genomic position above the detection threshold and the end of the second pulse is associated with a last genomic position above the detection threshold.

20. The method of claim 19, wherein the nucleic acid molecules undergo an amplification prior to the sequencing.

21. The method of claim 20, wherein the detection threshold is a number between 0.5 and 2.

22. The method of claim 19, wherein determining the genomic location of the pulse in the histogram further includes:
combining the first pulse with a second pulse when the end of the first pulse is within a length threshold of the beginning of the second pulse.

23. The method of claim 19, wherein the determining the set of continuous genomic positions with histogram values above the detection threshold uses average histogram values that are an average of raw histogram values within a window, wherein a raw histogram value is the number of instances that an aligned sequence includes a particular genomic position.

24. The method of claim 23, further comprising:
before calculating the average histogram values, identifying genomic positions having raw histogram values below a minimum threshold; and
for any genomic position with a raw histogram value below the minimum threshold, setting the raw histogram value to zero.

25. The method of claim 18, further comprising:
identifying incorrectly aligned sequences in the first chromosomal region; and
removing the incorrectly aligned sequences from any corresponding histograms.

26. A computer product comprising a computer readable medium storing a plurality of instructions for controlling a computer system to perform an operation of detecting a structural variation in a genome of a sample from an organism, the instructions comprising:
receiving sequence data from a sequencing of a plurality of nucleic acid molecules of the sample, the sequence data including sequences of at least one portion of each nucleic acid molecule of the plurality of nucleic acid molecules, wherein the sequencing is performed by:
providing a plurality of aliquots, each aliquot comprising nucleic acid molecules of the genome that have barcodes to track from which aliquot a nucleic acid molecule originates, wherein each of the plurality of aliquots includes less than a genomic equivalent of the genome of the organism;
sequencing a plurality of nucleic acid molecules in the plurality of aliquots to obtain sequences of the plurality of nucleic acid molecules and the barcodes, wherein the sequence data includes the barcodes for tracking from which aliquot a sequence originates;
for each of the plurality of nucleic acid molecules:
aligning at least one sequence of the nucleic acid molecule to a reference genome;
for each of the plurality of aliquots, calculating a histogram for a first chromosomal region by:
identifying a respective group of sequences as being derived from a same fragment of DNA based on the barcodes of the respective group of sequences corresponding to a same aliquot, the same fragment including at least a portion of the first chromosomal region;
for each genomic position of a plurality of genomic positions within the first chromosomal region:
aggregating a number of instances that an aligned sequence of the respective group includes the genomic position;
comparing the histograms to identify a common increase or decrease in the histograms within a same window of the first chromosomal region as a location of the structural variation in the first chromosomal region of the genome of the organism.

27. The computer product of claim 26, wherein the instructions further comprise:
identifying common increases and decreases in histograms of other chromosomal regions, wherein the first chromosomal region is identified as having a first decrease in the corresponding histograms;
correlating the first decrease in the first chromosomal region with a second increase in a second chromosomal region;
determining the first decrease and the second increase to be part of a same structural variation;
determining that the first chromosomal region and the second chromosomal region are proximal to each other in the genome of the organism.

28. The computer product of claim 27, wherein correlating the first decrease in the first chromosomal region with the second increase in the second chromosomal region includes:
determining a first value from a first number of fragments of DNA that include both the first decrease and the second increase; and
comparing the first value to a threshold to determine that a correlation does exist when the first value is greater than the threshold.

29. The computer product of claim 28, wherein comparing the first number to the threshold includes:
calculating a function of the first value to obtain a first result; and
comparing the first result to the threshold, wherein the function is a ratio of the first value divided by a total number of fragments used to determine the structural variations in the first and second chromosomal regions.

30. The computer product of claim 27, wherein correlating the first decrease in the first chromosomal region with a second increase in the second chromosomal region includes:
determining a number of pairs of arms reads from a same nucleic acid molecule that have:
a first arm read that aligns to the first chromosomal region; and
a second arm read that aligns to the second chromosomal region; and
comparing the first number to a threshold to determine that a correlation does exist when the first number is greater than the threshold.

31. The computer product of claim 27, wherein the instructions further comprise:
correlating a third increase in a third chromosomal region with a fourth decrease in a fourth chromosomal region;
determining the third decrease and the fourth increase to be part of a same structural variation, wherein the structural variation is an insertion of the third chromosomal region into the fourth chromosomal region; and
determining that the third chromosomal region and the fourth chromosomal region are proximal to each other in the genome of the organism.

32. The computer product of claim 26, wherein identifying the common increase or decrease as the location of the structural variation in the first chromosomal region of the genome of the organism includes:
calculating a measure of the common increase or decrease;
comparing the measure to a threshold; and
determining that a structural variation exits when the measure is greater than the threshold.

33. The computer product of claim 32, wherein calculating the measure of the common increase or decrease includes:
  aggregating the histograms exhibiting the common increase or decrease of the first chromosomal region to obtain a total histogram, wherein the calculating the measure uses values from the total histogram.

34. The computer product of claim 32, wherein calculating a measure of the common increase or decrease includes:
  obtaining a maximum value from one or more of the histograms;
  obtaining a minimum value from one or more of the histograms;
  calculating a difference between the maximum value and the minimum value; and
  comparing the difference to a difference threshold to determine if a structural variation exists.

35. The computer product of claim 26, wherein the instructions further comprise:
  determining when an aligned sequence of the respective group includes a particular genomic position by:
    receiving two arms reads of the aligned sequence, the two arm reads being aligned to the reference genome; and
    determining that the aligned sequence includes any genomic positions between the two arm reads.

36. The computer product of claim 26, wherein comparing the histograms to identify the common increase or decrease in the histograms within the same window of the first chromosomal region includes:
  determining a genomic location of a pulse in a histogram;
  identifying a beginning of the pulse as an increase in the histogram; and
  identifying an end of the pulse as a decrease in the histogram.

37. The computer product of claim 36, wherein determining the genomic location of the pulse in a histogram includes:
  determining a set of continuous genomic positions with histogram values above a detection threshold; and
  identifying the set as a first pulse, wherein the beginning of the first pulse is associated with a first genomic position above the detection threshold and the end of the second pulse is associated with a last genomic position above the detection threshold.

38. The computer product of claim 37, wherein the determining the set of continuous genomic positions with histogram values above the detection threshold uses average histogram values that are an average of raw histogram values within a window, wherein a raw histogram value is the number of instances that an aligned sequence includes a particular genomic position, wherein the instructions further comprise:
  before calculating the average histogram values, identifying genomic positions having raw histogram values below a minimum threshold; and
  for any genomic position with a raw histogram value below the minimum threshold, setting the raw histogram value to zero.

* * * * *